(12) United States Patent
Christopherson et al.

(10) Patent No.: US 12,172,012 B2
(45) Date of Patent: Dec. 24, 2024

(54) PERCUTANEOUS ACCESS FOR SYSTEMS AND METHODS OF TREATING SLEEP-RELATED DISORDERED BREATHING

(71) Applicant: Inspire Medical Systems, Inc., Golden Valley, MN (US)

(72) Inventors: Mark A. Christopherson, Golden Valley, MN (US); Quan Ni, Golden Valley, MN (US); John Rondoni, Golden Valley, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 1383 days.

(21) Appl. No.: 16/712,501

(22) Filed: Dec. 12, 2019

(65) Prior Publication Data

US 2020/0230404 A1     Jul. 23, 2020

Related U.S. Application Data

(63) Continuation of application No. 15/345,096, filed on Nov. 7, 2016, now Pat. No. 10,543,366, which is a
(Continued)

(51) Int. Cl.
*A61N 1/36* (2006.01)
*A61B 5/085* (2006.01)
(Continued)

(52) U.S. Cl.
CPC ............ *A61N 1/3601* (2013.01); *A61B 5/085* (2013.01); *A61N 1/0504* (2013.01); *A61N 1/0551* (2013.01); *A61N 1/0558* (2013.01); *A61N 1/37205* (2013.01); *A61B 5/0826* (2013.01); *A61B 5/296* (2021.01); *A61B 5/4818* (2013.01);
(Continued)

(58) Field of Classification Search
CPC .. A61N 1/3601; A61N 1/0504; A61N 1/0551; A61N 1/37205; A61N 1/0558; A61B 5/085; A61B 5/0826; A61B 17/3468
See application file for complete search history.

(56) References Cited

U.S. PATENT DOCUMENTS 4,154,247 A    5/1979  O'Neill
4,379,462 A    4/1983  Borkan et al.
(Continued)

FOREIGN PATENT DOCUMENTS

DE       10103288 A1     8/2002
JP       2005521490      7/2005
(Continued)

OTHER PUBLICATIONS

Medtronic, "Navigation Tracking Technologies", Medtronic website, Dec. 28, 2008, 1 page.
(Continued)

*Primary Examiner* — Pamela M. Bays
(74) *Attorney, Agent, or Firm* — Dicke, Billig & Czaja, PLLC

(57) ABSTRACT

A method of implanting includes inserting a stimulation element into a head-and-neck region and positioning an electrode array of the stimulation element relative to a target portion of a nerve.

7 Claims, 18 Drawing Sheets

Related U.S. Application Data continuation of application No. 13/262,434, filed as application No. PCT/US2010/029253 on Mar. 30, 2010, now Pat. No. 9,486,628.

(60) Provisional application No. 61/165,110, filed on Mar. 31, 2009.

(51) Int. Cl.
| | |
|---|---|
| *A61N 1/05* | (2006.01) |
| *A61N 1/372* | (2006.01) |
| *A61B 5/00* | (2006.01) |
| *A61B 5/08* | (2006.01) |
| *A61B 5/296* | (2021.01) |
| *A61B 17/34* | (2006.01) |
| *A61B 90/00* | (2016.01) |

(52) U.S. Cl.
CPC ..... *A61B 17/3468* (2013.01); *A61B 2090/062* (2016.02); *A61N 1/0553* (2013.01); *A61N 1/0556* (2013.01)

(56) References Cited

U.S. PATENT DOCUMENTS

| | | |
|---|---|---|
| 4,414,986 A | 11/1983 | Dickhudt et al. |
| 4,485,815 A | 12/1984 | Amplatz et al. |
| 4,512,351 A | 4/1985 | Pohndorf |
| 4,567,892 A | 2/1986 | Plicchi et al. |
| 4,573,481 A | 3/1986 | Bullara |
| 4,920,979 A | 5/1990 | Bullara |
| 4,960,133 A | 10/1990 | Hewson |
| 4,979,511 A | 12/1990 | Terry, Jr. |
| 5,016,808 A | 5/1991 | Heil, Jr. et al. |
| 5,105,826 A | 4/1992 | Smits et al. |
| 5,121,754 A | 6/1992 | Mullett |
| 5,146,918 A | 9/1992 | Kallok et al. |
| 5,158,080 A | 10/1992 | Kallok |
| 5,167,229 A | 12/1992 | Peckham et al. |
| 5,178,156 A | 1/1993 | Takishima et al. |
| 5,226,427 A | 7/1993 | Buckberg et al. |
| 5,230,338 A | 7/1993 | Allen et al. |
| 5,238,006 A | 8/1993 | Markowitz |
| 5,251,634 A | 10/1993 | Weinberg |
| 5,344,438 A | 9/1994 | Testerman et al. |
| 5,351,394 A | 10/1994 | Weinberg |
| 5,388,578 A | 2/1995 | Yomtov et al. |
| 5,505,201 A | 4/1996 | Grill, Jr. et al. |
| 5,524,632 A | 6/1996 | Stein et al. |
| 5,531,778 A | 7/1996 | Maschino et al. |
| 5,540,734 A | 7/1996 | Zabara |
| 5,560,372 A | 10/1996 | Cory |
| 5,591,216 A | 1/1997 | Testerman et al. |
| 5,957,965 A | 9/1999 | Moumane et al. |
| 6,015,389 A | 1/2000 | Brown |
| 6,025,624 A | 2/2000 | Figura |
| 6,041,780 A | 3/2000 | Richard et al. |
| 6,051,017 A | 4/2000 | Loeb et al. |
| 6,052,624 A | 4/2000 | Mann |
| 6,172,772 B1 | 1/2001 | Steinle et al. |
| 6,175,767 B1 | 1/2001 | Doyle, Sr. |
| 6,181,961 B1 | 1/2001 | Prass |
| 6,240,316 B1 | 5/2001 | Richmond et al. |
| 6,249,707 B1 | 6/2001 | Kohnen et al. |
| 6,251,126 B1 | 6/2001 | Ottenhoff et al. |
| 6,269,269 B1 | 7/2001 | Ottenhoff et al. |
| 6,309,401 B1 | 10/2001 | Redko et al. |
| 6,361,494 B1 | 3/2002 | Lindenthaler |
| 6,366,815 B1 | 4/2002 | Haugland et al. |
| 6,393,325 B1 | 5/2002 | Mann et al. |
| 6,449,507 B1 | 9/2002 | Hill et al. |
| 6,456,866 B1 | 9/2002 | Tyler et al. |
| 6,511,458 B2 | 1/2003 | Milo et al. |
| 6,535,759 B1 | 3/2003 | Epstein et al. |
| 6,542,776 B1 | 4/2003 | Gordon et al. |
| 6,587,725 B1 | 7/2003 | Durand et al. |
| 6,606,521 B2 | 8/2003 | Paspa et al. |
| 6,609,032 B1 | 8/2003 | Woods et al. |
| 6,647,289 B2 | 11/2003 | Prutchi |
| 6,651,652 B1 | 11/2003 | Ward |
| 6,654,634 B1 | 11/2003 | Prass |
| 6,718,208 B2 | 4/2004 | Hill et al. |
| 6,731,976 B2 | 5/2004 | Penn et al. |
| 6,805,667 B2 | 10/2004 | Christopherson et al. |
| 6,829,508 B2 | 12/2004 | Schulman et al. |
| 6,847,849 B2 | 1/2005 | Mamo et al. |
| 6,893,405 B2 | 5/2005 | Kumar et al. |
| 6,904,320 B2 | 6/2005 | Park et al. |
| 6,907,293 B2 | 6/2005 | Grill |
| 6,928,324 B2 | 8/2005 | Park |
| 6,936,011 B2 | 8/2005 | Sheldon |
| 6,971,393 B1 | 12/2005 | Mamo et al. |
| 6,978,171 B2 | 12/2005 | Goetz et al. |
| 6,999,819 B2 | 2/2006 | Swoyer et al. |
| 7,054,692 B1 | 5/2006 | Whitehurst et al. |
| 7,077,810 B2 | 7/2006 | Lange et al. |
| 7,082,331 B1 | 7/2006 | Park et al. |
| 7,082,336 B2 | 7/2006 | Ransbury et al. |
| 7,087,053 B2 | 8/2006 | Vanney |
| 7,104,965 B1 | 9/2006 | Jiang et al. |
| 7,117,036 B2 | 10/2006 | Florio |
| 7,128,717 B1 | 10/2006 | Thach et al. |
| 7,149,573 B2 | 12/2006 | Wang |
| 7,155,278 B2 | 12/2006 | King et al. |
| 7,160,255 B2 | 1/2007 | Saadat |
| 7,167,743 B2 | 1/2007 | Heruth et al. |
| 7,174,215 B2 | 2/2007 | Bradley |
| 7,177,702 B2 | 2/2007 | Wallace et al. |
| 7,186,220 B2 | 3/2007 | Stahmann et al. |
| 7,189,204 B2 | 3/2007 | Ni et al. |
| 7,200,440 B2 | 4/2007 | Kim et al. |
| 7,214,197 B2 | 5/2007 | Prass |
| 7,216,000 B2 | 5/2007 | Sieracki et al. |
| 7,231,260 B2 | 6/2007 | Wallace et al. |
| 7,252,640 B2 | 8/2007 | Ni et al. |
| 7,277,749 B2 | 10/2007 | Gordon et al. |
| 7,330,760 B2 | 2/2008 | Heruth et al. |
| 7,336,996 B2 | 2/2008 | Hartley et al. |
| 7,359,755 B2 | 4/2008 | Jones et al. |
| 7,366,562 B2 | 4/2008 | Dukesherer et al. |
| 7,366,572 B2 | 4/2008 | Heruth et al. |
| 7,395,113 B2 | 7/2008 | Heruth et al. |
| 7,437,197 B2 | 10/2008 | Harris et al. |
| 7,447,545 B2 | 11/2008 | Heruth et al. |
| 7,463,928 B2 | 12/2008 | Lee et al. |
| 7,463,934 B2 | 12/2008 | Tronnes et al. |
| 7,468,040 B2 | 12/2008 | Hartley et al. |
| 7,469,697 B2 | 12/2008 | Lee et al. |
| 7,473,227 B2 | 1/2009 | Hsu et al. |
| 7,491,181 B2 | 2/2009 | Heruth et al. |
| 7,510,531 B2 | 3/2009 | Lee et al. |
| 7,515,968 B2 | 4/2009 | Metzler et al. |
| 7,526,341 B2 | 4/2009 | Goetz et al. |
| 7,542,803 B2 | 6/2009 | Heruth et al. |
| 7,572,225 B2 | 8/2009 | Stahmann et al. |
| 7,590,455 B2 | 9/2009 | Heruth et al. |
| 7,591,265 B2 | 9/2009 | Lee et al. |
| 7,596,413 B2 | 9/2009 | Libbus et al. |
| 7,596,414 B2 | 9/2009 | Whitehurst et al. |
| 7,599,730 B2 | 10/2009 | Hunter et al. |
| 7,603,170 B2 | 10/2009 | Hatlestad et al. |
| 7,606,613 B2 | 10/2009 | Simon et al. |
| 7,610,094 B2 | 10/2009 | Stahmann et al. |
| 7,634,315 B2 | 12/2009 | Cholette |
| 7,644,714 B2 | 1/2010 | Atkinson et al. |
| 7,657,308 B2 | 2/2010 | Miles et al. |
| 7,662,105 B2 | 2/2010 | Hatlestad |
| 7,672,728 B2 | 3/2010 | Libbus et al. |
| 7,678,061 B2 | 3/2010 | Lee et al. |
| 7,680,538 B2 | 3/2010 | Durand et al. |
| 7,684,869 B2 | 3/2010 | Bradley et al. |
| 7,702,385 B2 | 4/2010 | Moffitt et al. |
| 7,717,848 B2 | 5/2010 | Heruth et al. |
| 7,720,541 B2 | 5/2010 | Stahmann et al. |

(56) References Cited

U.S. PATENT DOCUMENTS

| | | |
|---|---|---|
| 7,725,195 B2 | 5/2010 | Lima et al. |
| 7,725,198 B2 | 5/2010 | Cross, Jr. et al. |
| 7,726,209 B2 | 6/2010 | Ruotoistenmaki |
| 7,734,340 B2 | 6/2010 | De Ridder |
| 7,734,350 B2 | 6/2010 | Dubnov et al. |
| 7,742,819 B2 | 6/2010 | Moffitt |
| 7,747,323 B2 | 6/2010 | Libbus et al. |
| 7,751,880 B1 | 7/2010 | Cholette |
| 7,757,690 B2 | 7/2010 | Stahmann et al. |
| 7,775,993 B2 | 8/2010 | Heruth et al. |
| 7,783,353 B2 | 8/2010 | Libbus et al. |
| 7,792,583 B2 | 9/2010 | Miesel et al. |
| 7,792,590 B1 | 9/2010 | Pianca et al. |
| 7,809,442 B2 | 10/2010 | Bolea et al. |
| 7,818,063 B2 | 10/2010 | Wallace et al. |
| 7,853,322 B2 | 12/2010 | Bourget et al. |
| 7,881,798 B2 | 2/2011 | Miesel et al. |
| 7,908,013 B2 | 3/2011 | Miesel et al. |
| 7,917,230 B2 | 3/2011 | Bly |
| 7,942,822 B1 | 5/2011 | Koh |
| 7,957,797 B2 | 6/2011 | Bourget et al. |
| 7,957,809 B2 | 6/2011 | Bourget et al. |
| 7,979,128 B2 | 7/2011 | Tehrani et al. |
| 8,016,776 B2 | 9/2011 | Bourget et al. |
| 8,021,299 B2 | 9/2011 | Miesel et al. |
| 8,150,531 B2 | 4/2012 | Skelton |
| 8,160,711 B2 | 4/2012 | Tehrani et al. |
| 8,175,720 B2 | 5/2012 | Skelton et al. |
| 9,486,628 B2 | 11/2016 | Christopherson et al. |
| 2001/0010010 A1 | 7/2001 | Richmond et al. |
| 2002/0010495 A1 | 1/2002 | Freed et al. |
| 2002/0049479 A1 | 4/2002 | Pitts |
| 2002/0120188 A1 | 8/2002 | Brock |
| 2002/0128700 A1 | 9/2002 | Cross, Jr. |
| 2002/0156507 A1 | 10/2002 | Lindenthaler |
| 2002/0183817 A1 | 12/2002 | Van Venrooij et al. |
| 2003/0093128 A1 | 5/2003 | Freed et al. |
| 2003/0114895 A1 | 6/2003 | Gordon et al. |
| 2003/0114905 A1 | 6/2003 | Kuzma |
| 2003/0139789 A1 | 8/2003 | Tvinnereim et al. |
| 2003/0195571 A1 | 10/2003 | Burnes et al. |
| 2003/0216789 A1 | 11/2003 | Deem et al. |
| 2004/0015204 A1 | 1/2004 | Whitehurst et al. |
| 2004/0073272 A1 | 4/2004 | Knudson et al. |
| 2004/0111139 A1 | 6/2004 | McCreery |
| 2004/0116819 A1 | 6/2004 | Alt |
| 2004/0162499 A1 | 8/2004 | Nagai et al. |
| 2004/0215288 A1 | 10/2004 | Lee et al. |
| 2004/0230278 A1 | 11/2004 | Dahl et al. |
| 2004/0260310 A1 | 12/2004 | Harris |
| 2005/0004610 A1 | 1/2005 | Kim et al. |
| 2005/0010265 A1 | 1/2005 | Baru Fassio et al. |
| 2005/0042589 A1 | 2/2005 | Hatlestad et al. |
| 2005/0043772 A1 | 2/2005 | Stahmann et al. |
| 2005/0076908 A1 | 4/2005 | Lee et al. |
| 2005/0080348 A1 | 4/2005 | Stahmann et al. |
| 2005/0080461 A1 | 4/2005 | Stahmann et al. |
| 2005/0080472 A1 | 4/2005 | Atkinson et al. |
| 2005/0081847 A1 | 4/2005 | Lee et al. |
| 2005/0085865 A1 | 4/2005 | Tehrani |
| 2005/0085866 A1 | 4/2005 | Tehrani |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0101833 A1 | 5/2005 | Hsu et al. |
| 2005/0113710 A1 | 5/2005 | Stahmann et al. |
| 2005/0115561 A1 | 6/2005 | Stahmann et al. |
| 2005/0145246 A1 | 7/2005 | Hartley et al. |
| 2005/0159637 A9 | 7/2005 | Nelson et al. |
| 2005/0165457 A1 | 7/2005 | Benser et al. |
| 2005/0171576 A1 | 8/2005 | Williams et al. |
| 2005/0182457 A1 | 8/2005 | Thrope |
| 2005/0209513 A1 | 9/2005 | Heruth et al. |
| 2005/0209643 A1 | 9/2005 | Heruth et al. |
| 2005/0234439 A1 | 10/2005 | Underwood |
| 2005/0234523 A1 | 10/2005 | Levin et al. |
| 2005/0240238 A1 | 10/2005 | Mamo et al. |
| 2005/0251216 A1 | 11/2005 | Hill et al. |
| 2005/0261747 A1 | 11/2005 | Schuler et al. |
| 2005/0267380 A1 | 12/2005 | Poezevara |
| 2005/0267547 A1 | 12/2005 | Knudson et al. |
| 2005/0277844 A1 | 12/2005 | Strother et al. |
| 2005/0277999 A1 | 12/2005 | Strother et al. |
| 2005/0278000 A1 | 12/2005 | Strother et al. |
| 2006/0004429 A1 | 1/2006 | Mrva et al. |
| 2006/0052836 A1 | 3/2006 | Kim et al. |
| 2006/0058852 A1 | 3/2006 | Koh et al. |
| 2006/0064029 A1 | 3/2006 | Arad |
| 2006/0079802 A1 | 4/2006 | Jensen et al. |
| 2006/0095088 A1 | 5/2006 | De Ridder |
| 2006/0103407 A1 | 5/2006 | Kakizawa et al. |
| 2006/0135886 A1 | 6/2006 | Lippert et al. |
| 2006/0142815 A1 | 6/2006 | Tehrani et al. |
| 2006/0167497 A1 | 7/2006 | Armstrong et al. |
| 2006/0184204 A1 | 8/2006 | He |
| 2006/0212096 A1 | 9/2006 | Stevenson |
| 2006/0235484 A1 | 10/2006 | Jaxx et al. |
| 2006/0241708 A1 | 10/2006 | Boute |
| 2006/0247729 A1 | 11/2006 | Tehrani et al. |
| 2006/0259079 A1 | 11/2006 | King |
| 2006/0264777 A1 | 11/2006 | Drew |
| 2006/0266369 A1 | 11/2006 | Atkinson et al. |
| 2006/0271137 A1 | 11/2006 | Stanton-Hicks |
| 2006/0282127 A1 | 12/2006 | Zealear |
| 2006/0293720 A1 | 12/2006 | DiLorenzo |
| 2006/0293723 A1 | 12/2006 | Whitehurst et al. |
| 2007/0027482 A1 | 2/2007 | Paris et al. |
| 2007/0043411 A1 | 2/2007 | Foster et al. |
| 2007/0233204 A1 | 10/2007 | Lima et al. |
| 2007/0255379 A1 | 11/2007 | Williams et al. |
| 2008/0039904 A1 | 2/2008 | Bulkes et al. |
| 2008/0046055 A1 | 2/2008 | Durand et al. |
| 2008/0064977 A1 | 3/2008 | Kelleher et al. |
| 2008/0097187 A1 | 4/2008 | Gielen et al. |
| 2008/0103545 A1* | 5/2008 | Bolea ............... A61N 1/37229 607/42 |
| 2008/0103575 A1 | 5/2008 | Gerber |
| 2008/0109046 A1 | 5/2008 | Lima et al. |
| 2008/0109048 A1 | 5/2008 | Moffitt |
| 2008/0132802 A1 | 6/2008 | Ni et al. |
| 2008/0139930 A1 | 6/2008 | Weese et al. |
| 2008/0183187 A1 | 7/2008 | Bly |
| 2008/0183254 A1 | 7/2008 | Bly et al. |
| 2008/0269602 A1 | 10/2008 | Csavoy et al. |
| 2008/0294060 A1 | 11/2008 | Haro et al. |
| 2009/0024047 A1 | 1/2009 | Shipley et al. |
| 2009/0036947 A1 | 2/2009 | Westlund et al. |
| 2009/0062882 A1 | 3/2009 | Zhang et al. |
| 2009/0112116 A1 | 4/2009 | Lee et al. |
| 2009/0118787 A1 | 5/2009 | Moffitt et al. |
| 2009/0234427 A1 | 9/2009 | Chinn et al. |
| 2009/0270707 A1 | 10/2009 | Alfoqaha et al. |
| 2009/0287279 A1 | 11/2009 | Parramon et al. |
| 2009/0308395 A1 | 12/2009 | Lee et al. |
| 2009/0326408 A1 | 12/2009 | Moon |
| 2010/0010566 A1 | 1/2010 | Thacker et al. |
| 2010/0036285 A1 | 2/2010 | Govari et al. |
| 2010/0076536 A1 | 3/2010 | Merz et al. |
| 2010/0094379 A1 | 4/2010 | Meadows et al. |
| 2010/0125310 A1 | 5/2010 | Wilson et al. |
| 2010/0125314 A1 | 5/2010 | Bradley et al. |
| 2010/0125315 A1 | 5/2010 | Parramon et al. |
| 2010/0137931 A1 | 6/2010 | Hopper et al. |
| 2010/0137949 A1 | 6/2010 | Mazgalev et al. |
| 2010/0152553 A1 | 6/2010 | Ujhazy |
| 2010/0174341 A1 | 7/2010 | Bolea et al. |
| 2010/0198103 A1 | 8/2010 | Meadows et al. |
| 2010/0228317 A1 | 9/2010 | Libbus et al. |
| 2010/0241195 A1 | 9/2010 | Meadows et al. |
| 2010/0241207 A1 | 9/2010 | Bluger |
| 2010/0262210 A1 | 10/2010 | Parramon et al. |

(56) References Cited

U.S. PATENT DOCUMENTS

| | | | |
|---|---|---|---|
| 2011/0093036 | A1 | 4/2011 | Mashiach |
| 2011/0152965 | A1 | 6/2011 | Mashiach et al. |

FOREIGN PATENT DOCUMENTS

| | | | |
|---|---|---|---|
| JP | 2007528774 | | 10/2007 |
| WO | 2003082404 | A1 | 10/2003 |
| WO | 2004064634 | | 8/2004 |
| WO | 2005092432 | A1 | 10/2005 |
| WO | 2006047264 | A1 | 5/2006 |
| WO | 2006057734 | A1 | 6/2006 |
| WO | 2006102591 | A2 | 9/2006 |
| WO | 2007068284 | A1 | 6/2007 |
| WO | 2007114860 | A2 | 10/2007 |
| WO | 2007118090 | A2 | 10/2007 |
| WO | 2008048471 | A2 | 4/2008 |
| WO | 2009048580 | A1 | 4/2009 |
| WO | 2009048581 | A1 | 4/2009 |
| WO | 2009140636 | A2 | 4/2009 |
| WO | 2009135138 | A1 | 11/2009 |
| WO | 2009135140 | A1 | 11/2009 |
| WO | 2009135142 | A1 | 11/2009 |
| WO | 2010039853 | A1 | 4/2010 |
| WO | 2010059839 | A2 | 5/2010 |
| WO | 2010117810 | | 10/2010 |

OTHER PUBLICATIONS

Van Buyten, et al., "Percutaneous technique for the treatment of Trigeminal Neuralgia becomes more precise and safer with the use of new Electromagnetic (EM) Navigation Technology", Nov. 1994, 6 pages.

Medtronic, "Intracardiac Navigation System", Medtronic website, Dec. 17, 2009, 2 pages.
Medtronic, "The O-ARM Imaging System", Medtronic website, Dec. 28, 2008, 1 page.
Medtronic, Stealth Station S7, "See the Bigger Picture", Medtronic website, Apr. 2008, 2 pages.
Eisele Article—David W. Eisele, MD et al., "Tongue neuromuscular and direct hypoglossal nerve stimulation for obstructive sleep apnea," Otolaryngologic Clinics of North America, Otolayngol Clin N Am 36 (2003) 501-510 (10 pages).
Goodall Article—Eleanor V. Goodhall et al., "Position-Selective Activation of Peripheral Nerve Fibers with a Cuff Electrode," IEEE Transaction on Biomedical Engineering, vol. 43, No. 8, Aug. 1996, pp. 851-856.
Oliven Article—Arie Oliven et al., "Upper airway response to electrical stimulation of the genioglossus in obstructive sleep apnea," Journal of Applied Physiology, vol. 95, pp. 2023-2029, Nov. 2003, www.jap.physiology.org on Sep. 18, 2006. (8 pages).
Schwartz Article—Alan R. Schwartz MD et al., Theraputic Electrical Stimulation of the Hypoglossal Nerve in Obstructive Sleep Apnea, Arch Otolaryngol Head And Neck Surg., vol. 127, Oct. 2001, pp. 1216-1223. Copyright 2001 American Medical Association. (8 pages).
Park Article—Jung I. Park MD, PhD, "Preoperative Percutaneous Cranial Nerve Mapping in Head and Neck Surgery", American Medical Association, 2003, (6 pages).
Hu Article—Lianggang Hu et al., "Percutaneous Biphasic Electrical Stimulation for Treatment of Obstructive Sleep Apnea Syndrome", IEEE Transactions on Biomedical Engineering, vol. 55, No. 1, Jan. 2008, (7 pages).
Mann Article—Eric A. Mann, MD, PhD et al., "The Effect of Neuromuscular Stimulation of the Genioglossus on the Hypopharyngeal Airway," The American Laryngouogical, Rhinological and Otological Society, Inc., 2002, pp. 351-356.

* cited by examiner

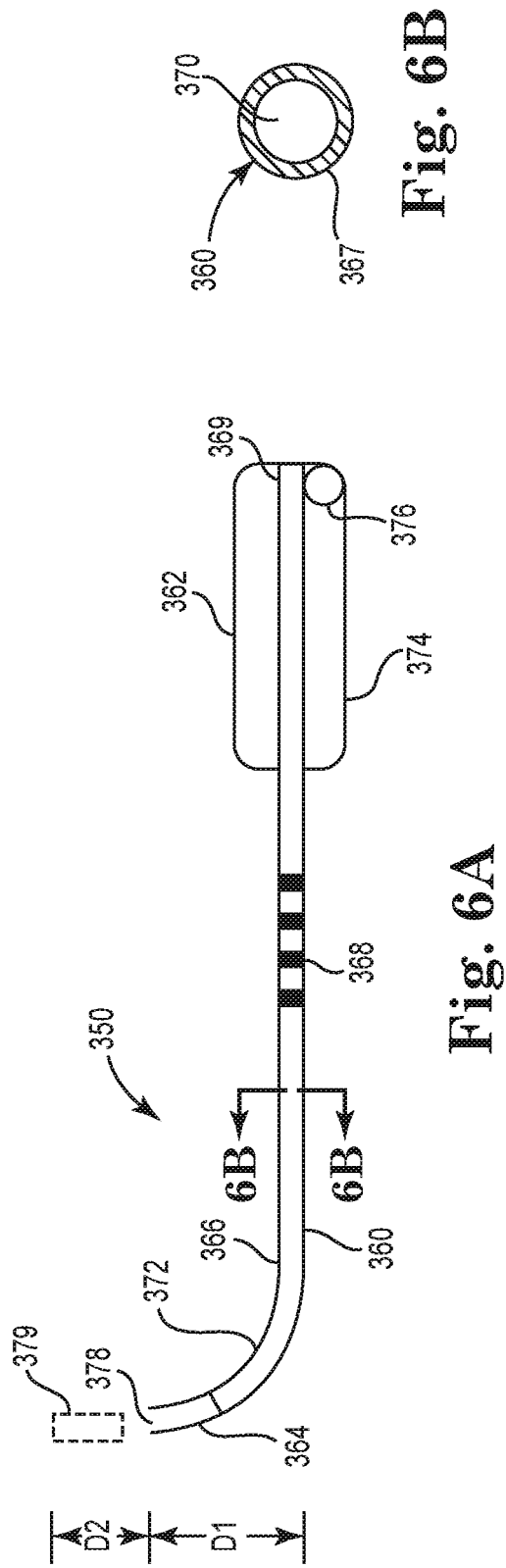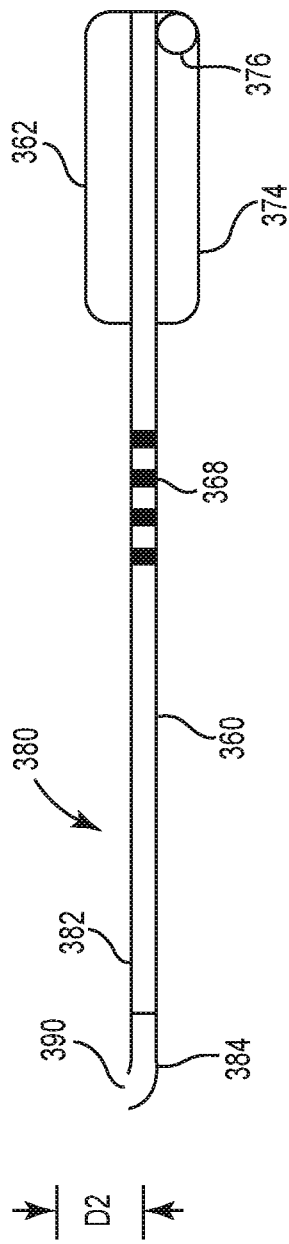

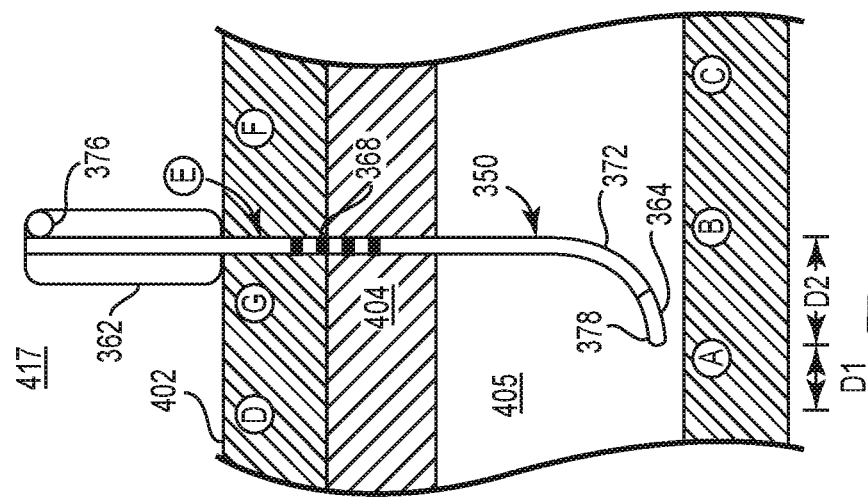
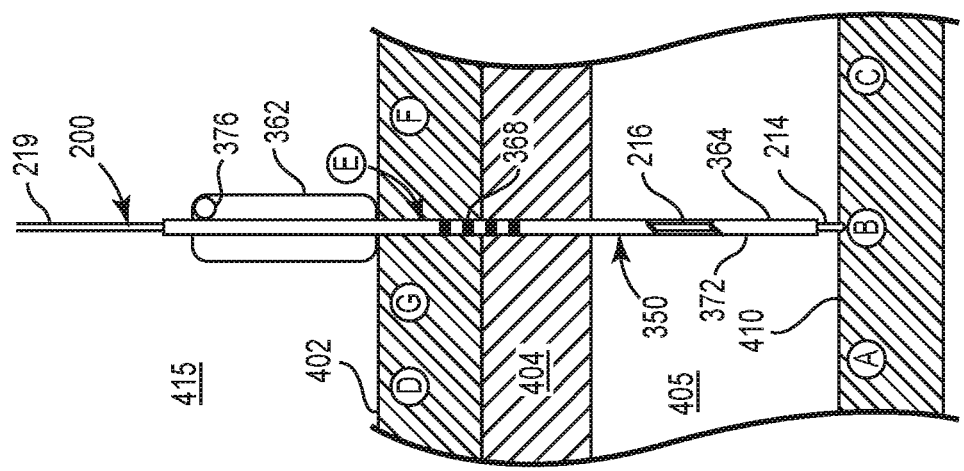
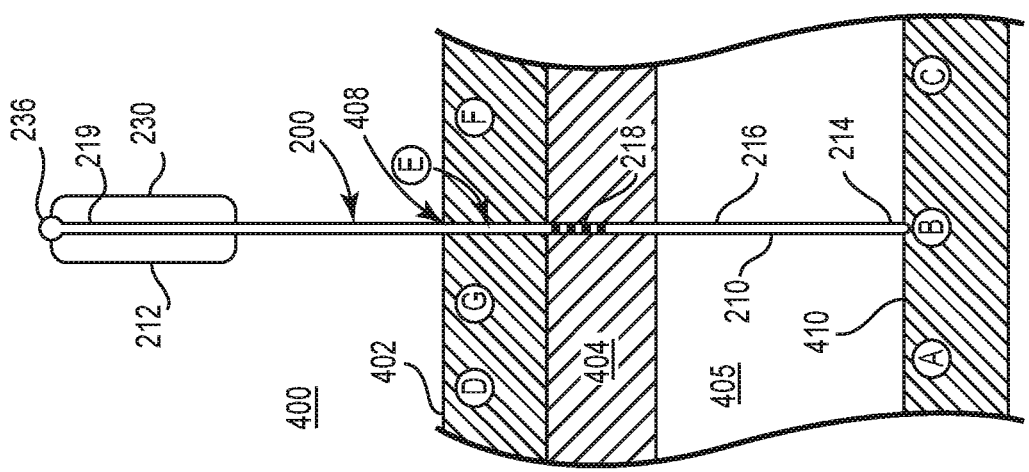

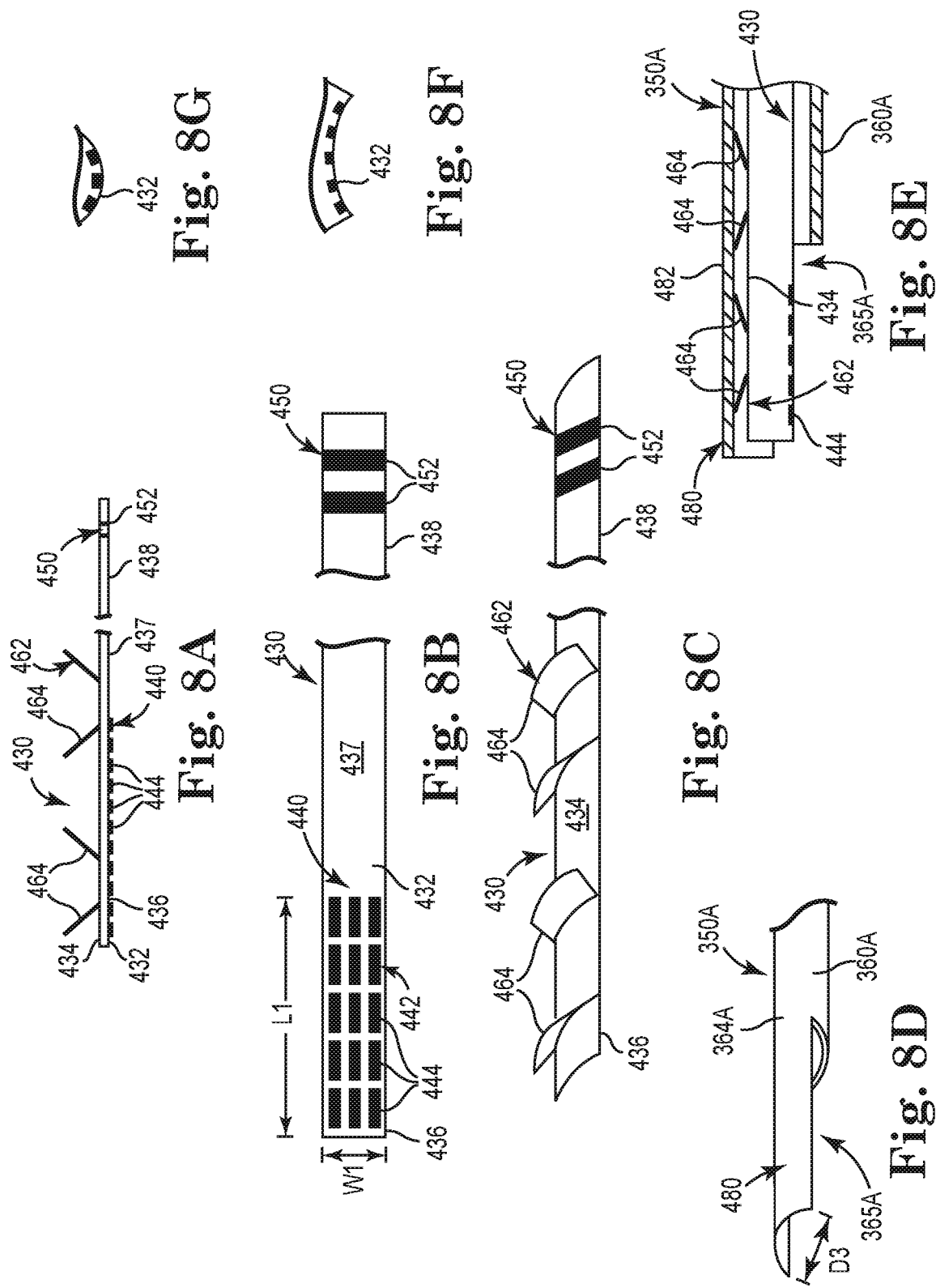

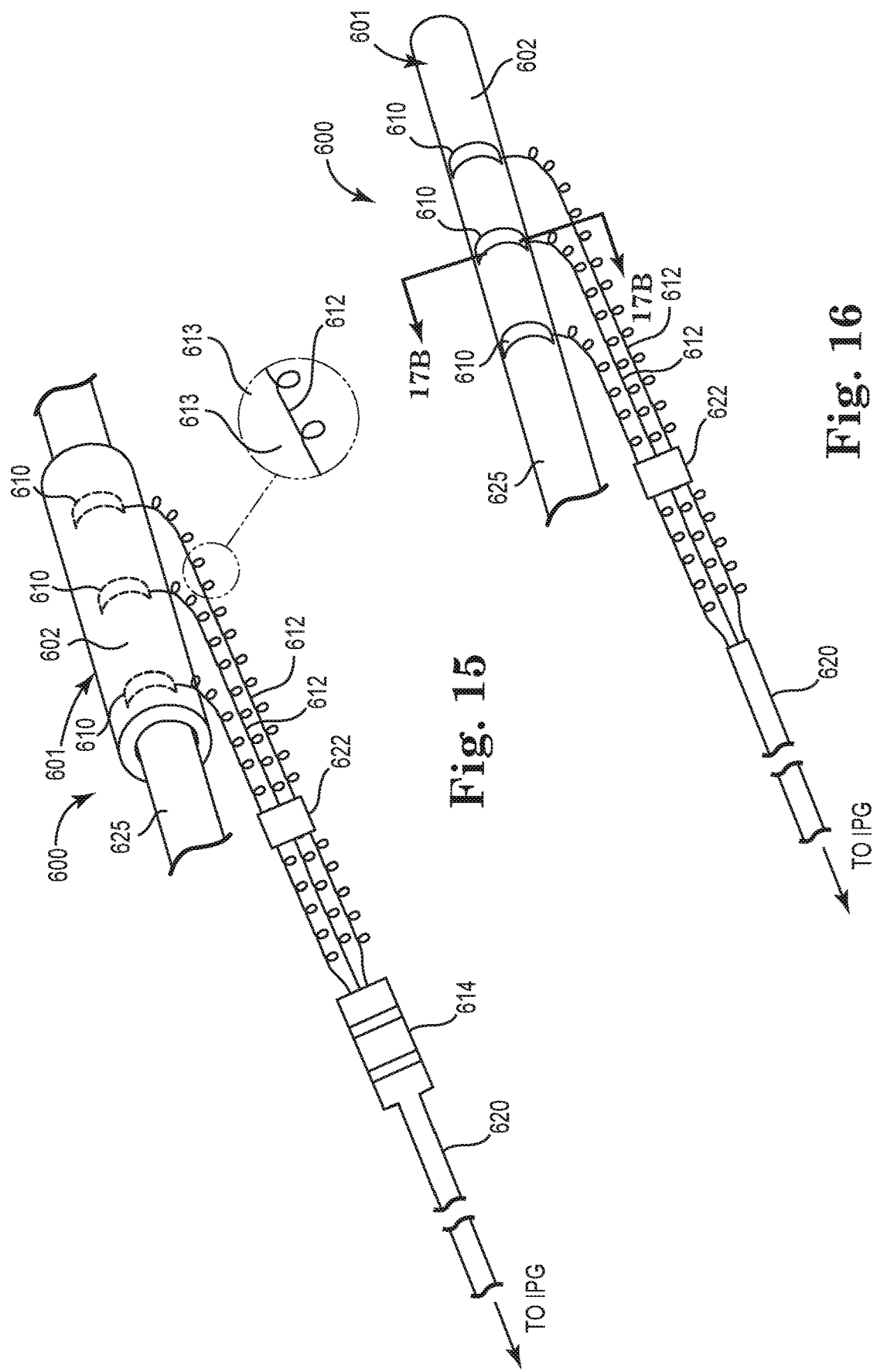

PERCUTANEOUS ACCESS FOR SYSTEMS AND METHODS OF TREATING SLEEP-RELATED DISORDERED BREATHING

CROSS-REFERENCE TO RELATED APPLICATIONS

This application is a Continuation of U.S. patent application Ser. No. 15/345,096, filed Nov. 7, 2016, now U.S. Pat. No. 10,543,366, which is a Continuation of U.S. patent application Ser. No. 13/262,434, filed Dec. 22, 2011, now U.S. Pat. No. 9,486,628, which is a 371 international application of PCT/US10/29253, filed Mar. 30, 2010, which claims the benefit of U.S. Provisional Patent Application Ser. No. 61/165,110, filed Mar. 31, 2009, all of which are incorporated herein by reference.

BACKGROUND

The present disclosure relates generally to an implantable stimulation system for stimulating and monitoring soft tissue in a patient, and more particularly, the present disclosure relates to systems and methods of using percutaneous delivery of a stimulation lead to treat sleep-related disordered breathing, such as obstructive sleep apnea and other disorders, and relates to various configurations of a stimulation electrode portion of a stimulation lead.

Sleep apnea generally refers to the cessation of breathing during sleep. One type of sleep apnea, referred to as obstructive sleep apnea (OSA), is characterized by repetitive pauses in breathing during sleep due to the obstruction and/or collapse of the upper airway, and is usually accompanied by a reduction in blood oxygenation saturation.

One treatment for obstructive sleep apnea has included the delivery of electrical stimulation to the hypoglossal nerve, located in the neck region under the chin. Such stimulation therapy activates the upper airway muscles to maintain upper airway patency. In treatment of sleep apnea, increased respiratory effort resulting from the difficulty in breathing through an obstructed airway is avoided by synchronized stimulation of an upper airway muscle or muscle group that holds the airway open during the inspiratory phase of breathing. For example, the genioglossus muscle is stimulated during treatment of sleep apnea by a cuff electrode placed around the hypoglossal nerve.

BRIEF DESCRIPTION OF THE DRAWINGS

Aspects and features of the present disclosure will be appreciated as the same becomes better understood by reference to the following detailed description of the embodiments of the present disclosure when considered in connection with the accompanying drawings, wherein:

FIG. 6A is a side plan view schematically illustrating a stimulation lead introduction tool, according to an embodiment of the present disclosure;

FIG. 6B is a sectional view as taken along lines 6B-6B of FIG. 6A, according to an embodiment of the present disclosure;

FIG. 6C is a side plan view schematically illustrating a stimulation lead introduction tool, according to an embodiment of the present disclosure;

FIG. 7A is sectional view schematically illustrating insertion of a test locator tool, according to an embodiment of the present disclosure;

FIG. 7B is sectional view schematically illustrating a configuration upon insertion of an introduction tool, according to an embodiment of the present disclosure;

FIG. 7C is sectional view schematically illustrating a configuration upon removal of a locator tool, according to an embodiment of the present disclosure;

FIG. 8A is a side plan view schematically illustrating a stimulation lead including a distal electrode portion, according to an embodiment of the present disclosure;

FIG. 8B is a bottom plan view of the stimulation lead of FIG. 8A including a schematic illustration of a stimulation electrode portion, according to an embodiment of the present disclosure;

FIG. 8C is a perspective view of the stimulation lead of FIGS. 8A-8B including a schematic illustration of an anchoring mechanism, according to an embodiment of the present disclosure;

FIG. 8D is a perspective view of a distal portion of a stimulation lead introduction tool, according to an embodiment of the present disclosure;

FIG. 8E is a sectional view of a distal portion of a stimulation lead introduction tool and a stimulation lead extending therethrough, according to an embodiment of the present disclosure;

FIG. 8F is partial end view of a distal portion of a stimulation lead having convex-shaped electrode portion, according to an embodiment of the present disclosure;

FIG. 8G is partial end view of a distal electrode portion of a stimulation lead having a concave-shaped electrode portion, according to an embodiment of the present disclosure;

FIG. 15 is a perspective view schematically illustrating a bio-absorbable stimulation system prior to absorption, according to an embodiment of the present disclosure;

FIG. 16 is a perspective view schematically illustrating the bio-absorbable stimulation system of FIG. 15 after absorption, according to an embodiment of the present disclosure;

FIG. 25 is a top plan view of an electrode portion of a stimulation lead, according to an embodiment of the present disclosure;

FIG. 26 is a top plan view schematically illustrating a stimulation system as deployed relative to a nerve, including the electrode portion of a stimulation lead and an insulator shield, according to an embodiment of the present disclosure;

FIG. 27 is a sectional view as taken along lines 27-27 of FIG. 26, according to an embodiment of the present disclosure;

FIG. 28 is a top plan view of an electrode portion of a stimulation lead, according to an embodiment of the present disclosure;

FIG. 29 is a side view schematically illustrating an insulator shield releasably connected, via a coupling mechanism, to an electrode portion of a stimulation lead, according to an embodiment of the present disclosure;

DESCRIPTION OF EMBODIMENTS

The following detailed description is merely exemplary in nature and is not intended to limit the present disclosure or the application and uses of the present disclosure. Furthermore, there is no intention to be bound by any expressed or implied theory presented in the preceding technical field, background, or the following detailed description.

Embodiments of the present disclosure provide implantable medical devices, systems, and methods for treating sleep-related disordered breathing, such as but not limited to obstructive sleep apnea. In these methods and systems, stimulation is provided to the hypoglossal nerve (or another target nerve) through a lead system that is delivered percutaneously or delivered using other minimally invasive techniques. In addition, embodiments of the present disclosure include various configurations of the stimulation electrode portion of a stimulation lead.

Figure 1:
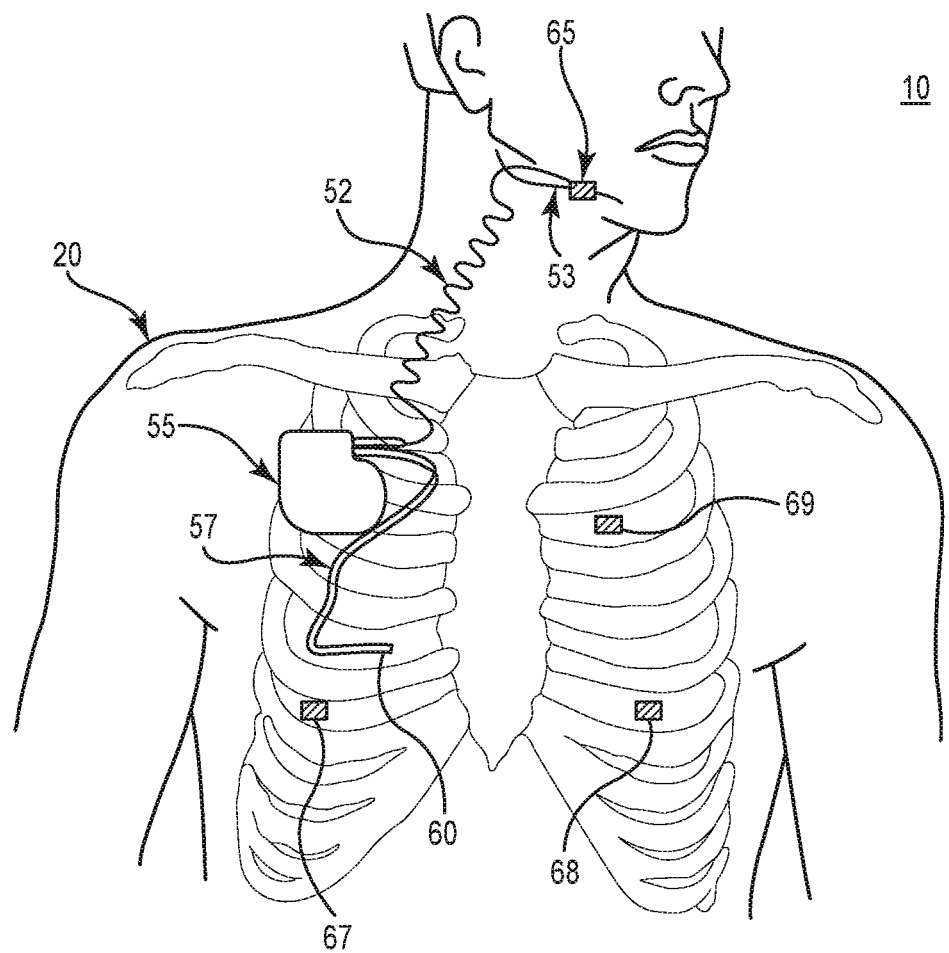
FIG. 1 is a schematic illustration of an implantable stimulation system, according to an embodiment of the present disclosure.

FIG. 1 is a schematic diagram of an implantable stimulation system that includes a percutaneously placed stimulation electrode, according to an embodiment of the present disclosure. As illustrated in FIG. 1, an example of an implantable stimulation system 10 according to one embodiment of the present disclosure includes an implantable pulse generator (IPG) 55, capable of being surgically positioned within a pectoral region of a patient 20, and a stimulation lead 52 electrically coupled with the IPG 55 via a connector (not shown) positioned within a connection port of the IPG 55. The lead 52 includes a stimulation electrode portion 65 and extends from the IPG 55 so that the stimulation electrode portion 65 is positioned in contact with a desired nerve, such as the hypoglossal nerve 53 of the patient 10, to enable stimulation of the nerve 53, as described below in detail. An exemplary implantable stimulation system in which lead 52 may be utilized, for example, is described in U.S. Pat. No. 6,572,543 to Christopherson et al., and which is incorporated herein by reference in its entirety. In one embodiment, the lead 52 further includes at least one sensor portion 60 (electrically coupled to the IPG 55 and extending from the IPG 55) positioned in the patient 10 for sensing respiratory effort, such as respiratory pressure.

In some embodiments, the sensor portion 60 detects respiratory patterns (e.g., inspiration, expiration, respiratory pause, etc.) in order to trigger activation of an electrode portion to stimulate a target nerve. Accordingly, with this arrangement, the IPG 55 (FIG. 1) receives sensor waveforms from the respiratory sensor portion 60, thereby enabling the IPG 55 to deliver electrical stimulation synchronously with inspiration (or another aspect of the respiratory pattern related to inspiration) according to a therapeutic treatment regimen in accordance with embodiments of the present disclosure. It is also understood that the respiratory sensor portion 60 is powered by the IPG 55 and the IPG 55 also contains internal circuitry to accept and process the impedance signal from the stimulation lead 52.

In some embodiments, the sensor portion 60 is a pressure sensor. In one aspect, the pressure sensor in this embodiment detects pressure in the thorax of the patient. In another aspect, the sensed pressure could be a combination of thoracic pressure and cardiac pressure (e.g., blood flow). With this configuration, the controller is configured to analyze this pressure sensing information to detect the respiratory patterns of the patient.

In some other embodiments, the respiratory sensor portion 60 comprises a bio-impedance sensor or pair of bio-impedance sensors and can be located in regions other than the pectoral region. In one aspect, such an impedance sensor is configured to sense a bio-impedance signal or pattern whereby the control unit evaluates respiratory patterns within the bio-impedance signal. For bio-impedance sensing, in one embodiment, electric current will be injected through an electrode portion within the body and an electrically conductive portion of a case of the IPG 55 (FIG. 3A) with the voltage being sensed between two spaced apart stimulation electrode portions (or also between one of the stimulation electrode portions and the electrically conductive portion of the case of IPG 55) to compute the impedance.

In some embodiments, system 10 also comprises additional sensors to further obtain physiologic data associated with respiratory functions. For example, system 10 may include various sensors (e.g., sensors 67, 68, 69 in FIG. 1) distributed about the chest area for measuring a transthoracic bio-impedance signal, an electrocardiogram (ECG) signal, or other respiratory-associated signals.

In some embodiments, the sensing and stimulation system for treating obstructive sleep apnea is a totally implantable system which provides therapeutic solutions for patients diagnosed with obstructive sleep apnea. In other embodiments, one or more components of the system are not implanted in a body of the patient. A few non-limiting examples of such non-implanted components include external sensors (respiration, impedance, etc.), an external processing unit, or an external power source. Of course, it is further understood that the implanted portion(s) of the system provides a communication pathway to enable transmission of data and/or controls signals both to and from the implanted portions of the system relative to the external portions of the system. The communication pathway includes a radiofrequency (RF) telemetry link or other wireless communication protocols.

Whether partially implantable or totally implantable, the system is designed to stimulate the hypoglossal nerve during inspiration to thereby prevent obstructions or occlusions in the upper airway during sleep. In one embodiment, the implantable system comprises an implantable pulse generator (IPG), a peripheral nerve cuff stimulation lead, and a pressure sensing lead.

Figure 2:
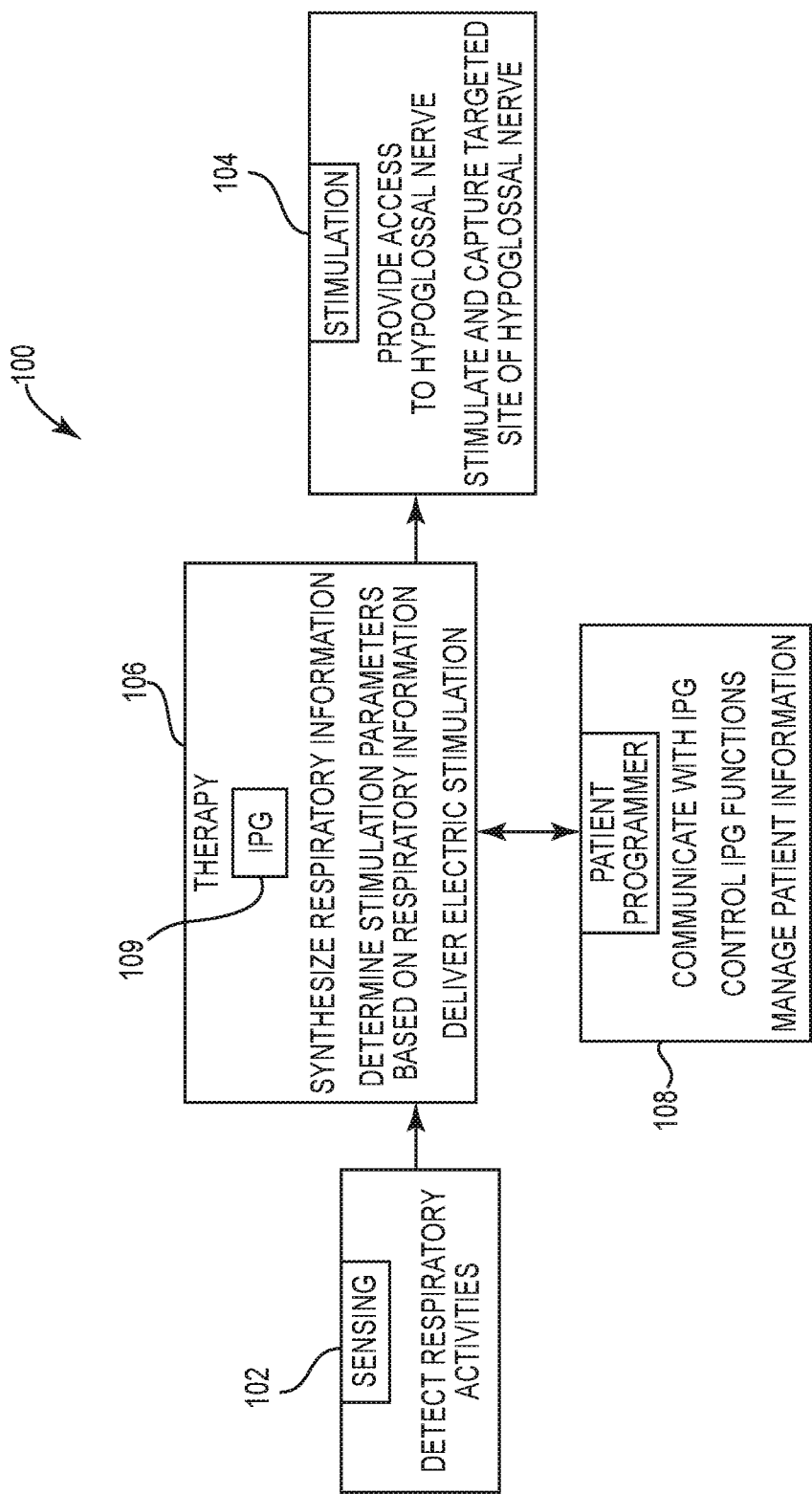
FIG. 2 is a schematic illustration of a block diagram of an implantable stimulation system, according to an embodiment of the present disclosure.

FIG. 2 is a block diagram schematically illustrating an implantable stimulation system 100, according to one embodiment of the present disclosure. In one embodiment, system 100 comprises at least substantially the same features and attributes as system 10 of FIG. 1. As illustrated in FIG. 2, system 100 includes a sensing module 102, a stimulation module 104, a therapy module 106, and a patient management module 108. In one embodiment, the IPG 109 of therapy module 106 comprises at least substantially the same features and attributes as IPG 55 of FIG. 1.

Via an array of parameters, the sensing module 102 receives and tracks signals from various physiologic sensors (such as a pressure sensor, blood oxygenation sensor, acoustic sensor, electrocardiogram (ECG) sensor, or impedance sensor) in order to determine a respiratory state of a patient, whether or not the patient is asleep or awake, and other respiratory-associated indicators, etc. Such respiratory detection may be received from either a single sensor or any multiple of sensors, or combination of various physiologic sensors which may provide a more reliable and accurate signal.

Figure 3:
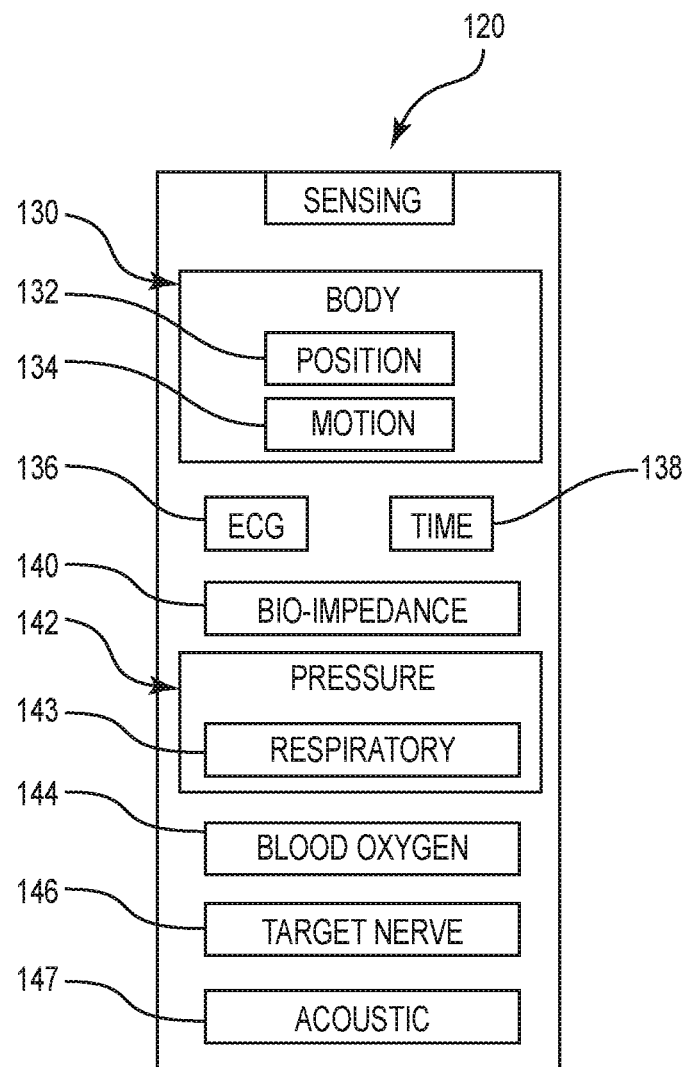
FIG. 3 is a schematic illustration of a block diagram of a sensing monitor, according to an embodiment of the present disclosure.

For example, in one embodiment, the sensing module 102 comprises a sensing monitor 120, as illustrated in FIG. 3. The sensing monitor 120 includes a body parameter 130, which includes at least one of a position-sensing component 132 or a motion-sensing component 134. In one embodiment, the motion-sensing component 134 tracks sensing of "seismic" activity (via an accelerometer or a piezoelectric transducer) that is indicative of walking, body motion, talking, etc. In another embodiment, the position-sensing component 132 tracks sensing of a body position or posture via an accelerometer or other transducer. In some embodiments, body parameter 130 utilizes signals from both the position-sensing component 132 and the motion-sensing component 134.

In some embodiments, sensing monitor 120 additionally comprises one or more of the following parameters: an ECG parameter 136; a time parameter 138; a bio-impedance parameter 140; a pressure parameter 142; and a blood oxygen parameter 144. In one aspect, the pressure parameter 142 includes a respiratory pressure component 143. In one aspect, the time parameter 142 tracks time generally (e.g. time intervals, elapsed time, etc.) while in other aspects, the time parameter 142 tracks the time of day in addition to or instead of the general time parameters. In another aspect, the time parameter 142 can be used to activate or deactivate a therapy regimen according to a time of day.

It is also understood that system 100 (FIG. 2) would include, or be connected to, the analogous physiologic sensor (e.g., LED-type or optical tissue perfusion oxygen saturation) implanted within or attached to the body of the patient to provide data to each one of their respective parameters (e.g., blood oxygenation parameter 144) of the sensing monitor 120. In some embodiments, sensing monitor 120 also includes a target nerve parameter 146 which represents physiologic data regarding the activity of a nerve to be stimulated, such as the hypoglossal nerve, including specification of the trunk and/or one or more branches of the hypoglossal nerve. In yet other embodiments, sensing monitor 120 also includes an acoustic sensing parameter 147 which represents physiologic data from respiratory airflow or cardiac activity that is sensed acoustically and that is indicative of respiratory effort.

In further reference to FIG. 2, therapy manager 106 of system 100 is configured to automatically control initiation, termination, and/or adjustment of a sleep apnea therapy, in accordance with the principles of the present disclosure. Therapy manager 106 also tracks and applies various treatment parameters, such as an amplitude, pulse width, electrode polarity, duration, and/or frequency of a neuro-stimulation signal, in accordance with a treatment protocol programmed into the therapy manager 106.

In one embodiment, therapy manager 106 comprises one or more processing units and associated memories configured to generate control signals directing the operation of system 100, including at least sensing module 102, therapy manager 106, stimulation module 104, and patient management module 108. In particular, in response to or based upon commands received via an input and/or instructions contained in the memory associated with the controller in response to physiologic data gathered via the sensing module 102, therapy manager 106 generates control signals directing operation of stimulation module 104 to selectively control stimulation of a target nerve, such as the hypoglossal nerve, to restore airway patency and thereby reduce or eliminate apnea events.

With this in mind, therapy manager 106 acts to synthesize respiratory information, to determine suitable stimulation parameters based on that respiratory information, and to direct electrical stimulation to the target nerve. While any number of physiologic parameters can be used with varying success to detect an apnea, in one embodiment of the present disclosure, the sensing module 102 detects apneas via a thoracic bio-impedance parameter. In particular, a measurement of thoracic impedance is used to track the relative amplitude of the respiratory waveform. Physiologically speaking, the bio-impedance of the lungs varies as the lungs fill and empty with air. Accordingly, thoracic impedance increases during inspiration and decreases during expiration. In another aspect, a varying respiratory drive will also cause the amplitude of the bio-impedance to vary, with a larger respiratory drive increasing the signal amplitude of the bio-impedance.

Upon obtaining the bio-impedance signal, the bio-impedance signal is further processed to identify an average peak amplitude over time. An apnea is detected by further identifying cyclic amplitude variations that occur for a duration substantially similar to the already known duration of a typical apnea event.

For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage, as represented by a memory associated with the controller. In other embodiments, hard wired circuitry may be used in place of or in combination with software instructions to implement the functions described. For example, the controller may be embodied as part of one or more application-specific integrated circuits (ASICs). Unless otherwise specifically noted, the controller is not limited to any specific combination of hardware circuitry and software, nor limited to any particular source for the instructions executed by the processing unit.

In general terms, the stimulation module 104 of system 100 is configured to generate and apply a neuro-stimulation signal via electrode(s) (such as stimulation electrode(s) 65) according to a treatment regimen programmed by a physician and/or in cooperation with therapy manager 106.

In general terms, the patient management module 108 is configured to facilitate communication to and from the IPG 109 in a manner familiar to those skilled in the art. Accordingly, the patient management module 108 is configured to report activities of the IPG 109 (including sensed physiologic data, stimulation history, number of apneas detected, etc.) and is configured to receive initial or further programming of the IPG 109 from an external source, such as a patient programmer, clinician programmer, etc.

Figure 4:
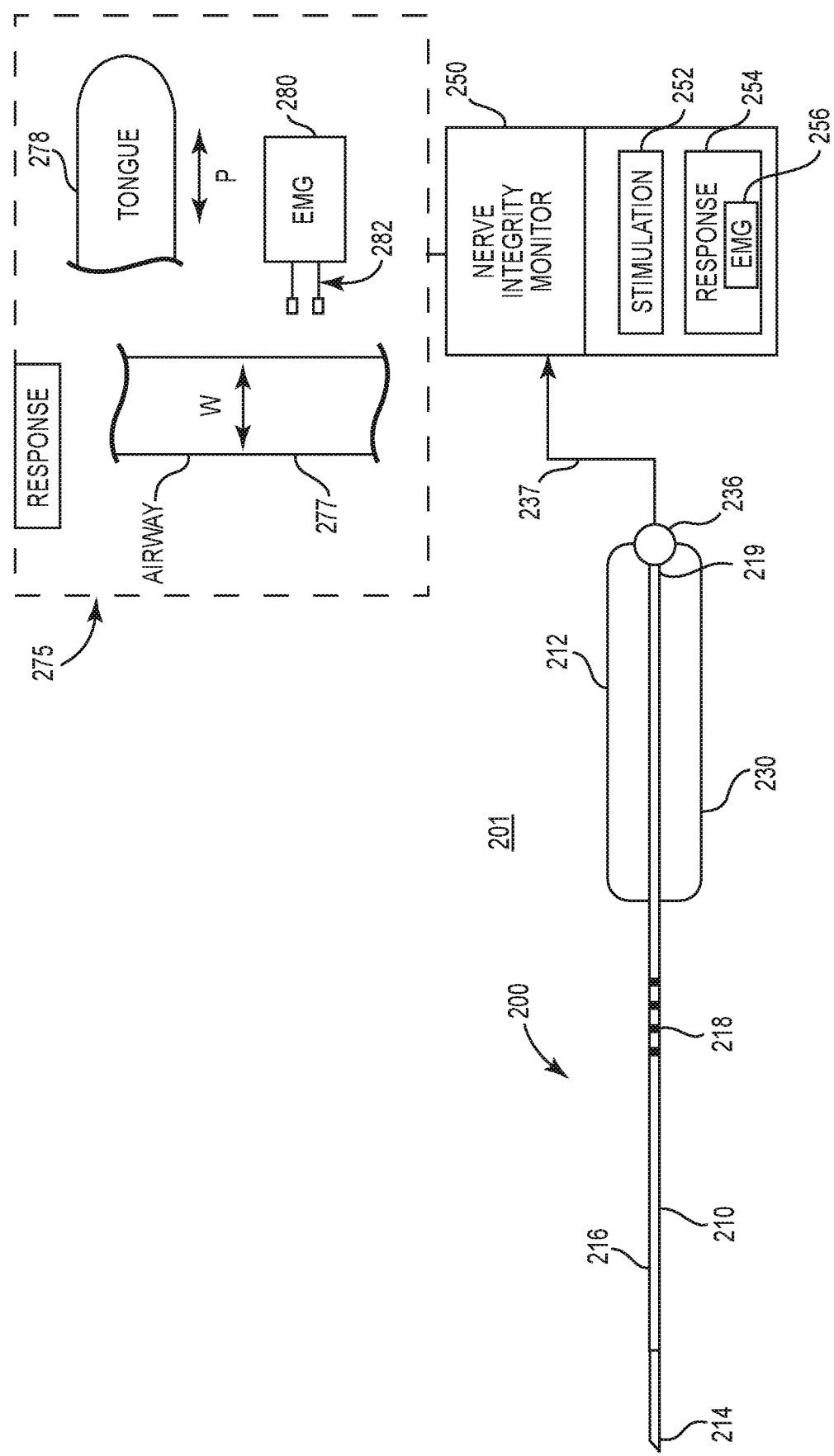
FIG. 4 is a schematic illustration of a percutaneous access system including a site locator tool, a stimulation monitor, and a response evaluation array, according to an embodiment of the present disclosure.

In accordance with at least one embodiment of the present disclosure, a stimulation site locator tool 200 of a percutaneous delivery system 201 is schematically illustrated in the plan view of FIG. 4. In general terms, the site locator tool 200 is configured to facilitate identifying a target or optimal stimulation site and/or a point of penetration to perform a percutaneous delivery of a stimulation lead near the target stimulation site. As shown in FIG. 4, site locator tool 200 includes a needle 210 extending from a handle 212. The needle 210 includes a distal tip 214, needle body 216, and a series of depth markers 218 extending along the needle body 216. The needle 210 extends proximally from the distal tip 214 and through handle 212, terminating at proximal end 219. At proximal end 219, a connection port 236 provides releasable electrical connection between the needle 210 and a stimulation monitor (as later described in more detail), which provides an electrical stimulation signal at distal tip 214.

Referring again to FIG. 4, in one aspect, the needle body 216 includes a dielectric coating on its outer surface while a conductive surface of the distal tip 214 is exposed to allow electrical conductivity between the distal tip 214 and the tissue within the body. The depth markers 218 are visible to the eye and may in some embodiments, be formed of a material that is readily visible through radiographic and/or ultrasound visualization techniques, as later described in more detail.

Moreover, it is understood that various surgical visualization techniques can be used in association with the embodiments of the present disclosure to assist in determining the location of the site locator tool 200, the stimulation electrode portion, and other components involved in percutaneous delivery of the stimulation lead.

By inserting the site locator tool 200 percutaneously at various locations near or adjacent to the hypoglossal nerve (in cooperation with a stimulation monitor) the path of the hypoglossal nerve is identified based on the type and magnitude of neurogenic responses, such as neuromuscular responses, observed upon application of the test stimulation signal at those various test locations. In this way, those test locations that exhibit a neuromuscular response indicative of a quality nerve capture are used to identify the optimal or target site to place a stimulation electrode portion of a stimulation lead. These observed responses are also used to identify a skin insertion point at which the percutaneous access will be initiated.

In some embodiments, the neuro-stimulation signal is applied at a single stimulation site along the hypoglossal nerve as illustrated in FIG. 1 (see stimulation electrode portion 65). However, in other embodiments, the neuro-stimulation signal of a sleep apnea therapy is applied from two or more of multiple locations spaced longitudinally along the hypoglossal nerve. In such an arrangement, the separate, spaced apart stimulation electrode portions can be activated simultaneously or activated at different times. With this in mind, it is understood that the percutaneous access method can be applied to locate more than one site along the hypoglossal nerve to identify placement of several different stimulation electrode portions.

In further reference to FIG. 4, in cooperation with the site locator tool 200 a stimulation monitor, such as a nerve integrity monitor 250 (a stand alone monitor or a monitor integrated into a sleep apnea physician programmer 108, such as programmer 108 in FIG. 2), is connected to the site locator tool 200 via connector 237. The stimulation monitor is used to aide the physician in determining proper electrode placement via stimulation applied via the site locator tool 200. In one embodiment, an IPG 55 (FIG. 1) or IPG 109 (FIG. 2) can be used as the stimulation monitor. In some embodiments, the stand-alone nerve integrity monitor 250 comprises at least substantially the same features and attributes as the nerve integrity monitor described in U.S. Pat. No. 6,334,068, entitled INTRAOPERATIVE NEURO-ELECTROPHYSIOLOGICAL MONITOR, issued on Dec. 25, 2001, and which is hereby incorporated by reference in its entirety. In other embodiments, other nerve integrity monitors or an equivalent array of instruments (e.g., a stimulation probe and electromyography system) are used to apply the stimulation signal and evaluate the response of the muscle innervated by the target nerve.

As shown in FIG. 4, in some embodiments nerve integrity monitor 250 comprises stimulation module 252 and a response module 254 that includes electromyography monitoring electronics (EMG) 256. In addition, FIG. 4 further illustrates a response evaluation array 275, according to one embodiment of the present disclosure. The response evaluation array 275 provides one or more mechanisms to evaluate the effectiveness of a target site for stimulating a target nerve and to identify an entry point for percutaneous delivery of the stimulation electrode portion. In one embodiment, upon stimulation applied at a potential target site, the response array 275 includes: (1) observing or measuring the extent and location (an extension of the base of the tongue is preferred over extension of the tip) of tongue protrusion 278 (indicated by arrow P); (2) observing or measuring the extent of increased cross-sectional area (indicated by arrow W) of an upper respiratory airway 277, with the observation/measurement being performed via endoscopy, ultrasound, or other visualization techniques; and/or (3) measuring the extent of an EMG response 280 (measured via EMG electronics 256 of monitor 250) of one or more muscles.

Accordingly, with this in mind, monitor 250 and one or more aspects of the response array 275 are used to evaluate the positioning of site locator tool 200 relative to a potential stimulation site on a target nerve. In one aspect, a repetitive stimulation pattern is applied from the stimulation module 252 of nerve integrity monitor 250 to the distal tip 214 of site locator tool 200, as the site locator tool 200 is percutaneously inserted into various locations adjacent to the target nerve and into the target nerve. In some embodiments, the applied stimulation pattern is a 1 second burst of stimulation every 3 seconds, a ramping stimulation pattern, and/or a physician controlled burst. In another aspect, electromyography (EMG) monitoring electronics 256 of the nerve integrity monitor 250 enables measuring a muscle response to the nerve stimulation applied during the iterative percutaneous insertion of the site locator tool 200. Accordingly, as further shown in FIG. 4, fine wire electrodes 282 (or similar) are connected in electrical communication with EMG electronics 256 of the nerve integrity monitor 250 and are used to continuously monitor the muscle activity in response to the stimulation patterns applied via site locator tool 200. Using this arrangement, this closed loop feedback will allow the physician to obtain real-time feedback of a position of the site locator tool 200 (relative to the hypoglossal nerve) and feedback regarding the expected ability of a percutaneously implanted electrode lead to capture the target nerve.

Figure 5:
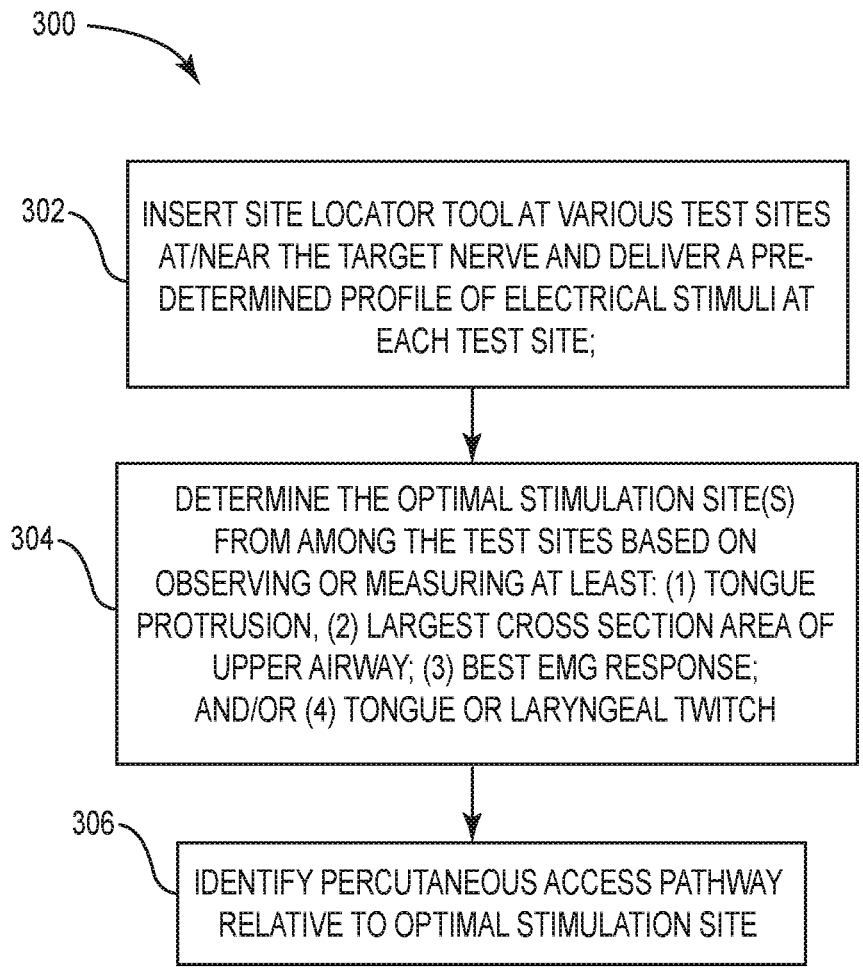
FIG. 5 is a schematic illustration of a method of identifying a stimulation site, according to an embodiment of the present disclosure.

In one embodiment of the present disclosure, as illustrated in FIG. 5, a method 300 of treating apnea includes identifying an optimal site to locate stimulation electrode portion 65 (FIG. 1) along a length of the hypoglossal nerve that will result in a desired stimulation of the hypoglossal nerve and treatment of sleep apnea. In particular, as illustrated at 302 in FIG. 5, the site locator tool 200 is inserted percutaneously (through the skin toward the target nerve) into various test stimulation sites at or around the hypoglossal nerve. For example, as further shown in the diagram 400 of FIG. 7A, needle 210 extends through percutaneous access path 408 such that distal tip 214 becomes electrically coupled relative to nerve 410 at one of several potential stimulation sites (e.g., A, B, C) with proximal handle 212 external to skin surface 402. Via surgical navigation techniques, the graduation markers 218 enable measuring a depth of insertion through skin 402 and other subcutaneous tissues 404, 405 surrounding nerve 410. While FIGS. 4 and 7A illustrate just a few such markers 218 for illustrative purposes, it will be understood that markers 218 would extend along a length or substantial length of needle 210 and that the spacing of such markers 218 may vary from that shown in FIGS. 4 and 7A. It will be understood that various components of tool 200 and the surrounding tissues are enlarged and/or minimized for illustrative purposes.

At each test site, a pre-determined profile of electrical stimuli is applied to identify one or more optimal or preferred target sites on the hypoglossal nerve. As illustrated at 304 in FIG. 5, the optimal or preferred target site are identified from among the test sites based observing or measuring at least: (1) a degree of tongue protrusion; (2) the size of cross-sectional area of the upper airway; (3) a best EMG response indicative of maintaining airway patency; (4) a lack of response from non-target muscles; and/or (5) a twitch from the tongue muscle and/or laryngeal muscle. In one aspect, an optimal or preferred target stimulation site is correlated with the greatest impact on maintaining airway patency during inspiration. After identifying a target site, method 300 includes identifying a percutaneous access pathway to the target site. In one aspect, this identification includes identifying a skin entry site (such as D, E, F, or G), which may or may not be directly above the target stimulation site on the hypoglossal nerve. Finally, it is understood that these steps 302-306 can be repeated iteratively, as necessary, until all the optimal stimulation locations along the target nerve are identified.

In one aspect, in evaluating various test stimulation sites, it will be understood that the magnitude of the measured response will be indicative how close the site locator tool 200 is to the hypoglossal nerve and/or which part of the hypoglossal nerve is being stimulated. For example, the distance between the site locator tool 200 and the hypoglossal nerve and the strength of the measured response is expressed in decreasing exponential relationship. In other words, as the distance away from the hypoglossal nerve increases, there is an exponential decrease in the magnitude of the measured response. In one aspect, the distance refers to a distance measured in three dimensions relative to the path of the hypoglossal nerve, as any given test site will involve: a lateral distance extending generally perpendicular relative to a longitudinal axis of the target nerve; (2) a vertical distance relative to the target nerve; and (3) a longitudinal distance extending generally parallel relative to a longitudinal axis of the target nerve. With this in mind, it is understood that as multiple potential sites are tested, a pattern is identified that highlights the best or optimal stimulation site(s) from among the test sites. In addition, other surgical navigation techniques can be used in cooperation with the application of the test stimulus to further pinpoint the optimal/preferred stimulation sites via visualizing the site locator tool 200 within the target anatomical environment at the time that the responses are measured.

In some embodiments, in evaluating multiple potential stimulation sites along the hypoglossal nerve, at each potential stimulation site the method 300 applies the pre-determined electrical stimuli as a stimulation signal with differing values for each signal parameter (e.g., pulse width, electrode polarity, frequency, duration, and amplitude) to determine which combination of values yields the best impact of the stimulation signal upon the target nerve at a potential site. In this way, each potential site is evaluated under conditions in which the stimulation signal would actually be applied were that potential site chosen as an optimal site for stimulation. In one embodiment, this determination of an optimal stimulation site via evaluating each of the stimulation parameters employs therapy module 106 (including IPG 109) in cooperation with stimulation module 104, a site locator tool 200, and patient programming module 108, as previously described in association with FIGS. 1-4.

In one aspect, an optimal stimulation site identified via the site locator tool 200 is preserved to allow an accurate delivery of the stimulation electrode portion of the stimulation lead to that site. Accordingly, in some embodiments, while maintaining needle 210 in its inserted position in the optimal site along the hypoglossal nerve, handle 212 is removed from needle body 216 while maintaining the distal tip 214 in a coupled relationship to nerve 410, and then a lead introduction tool is slidably advanced over the proximal portion 219 of needle 210 of site locator tool 200 to produce the configuration shown in FIG. 7B, as will be further described later.

In general terms, a stimulation lead is inserted percutaneously to result in a distal portion of the stimulation lead being closely adjacent to a target stimulation site of a nerve. In some embodiments, an introducing mechanism is used to initiate and develop a percutaneous access pathway to the target stimulation site and facilitates introduction of the stimulation lead therethrough. While various different shapes and forms of lead introduction tools can be used, FIG. 6A illustrates one exemplary embodiment of a lead introduction tool 350. As shown in FIG. 6A, lead introduction tool 350 includes a cannula 360 extending through and supported by handle 362. Cannula 360 includes a curved distal portion 375 with a body portion 366 extending proximally from distal portion 375 to a proximal portion 369 within handle 362. In one aspect, cannula 360 includes a series of graduation depth markers 368 to permit measurement of the desired depth of insertion. While FIGS. 6A and 7B illustrate just a few such markers 368 for illustrative purposes, it will be understood that markers 368 would extend along a length or substantial length of cannula 360 and that the spacing of such markers 368 may vary from that shown in FIGS. 6A and 7B. In some embodiments, at least some of the depth markers 368 are also formed of a radiopaque material to enable visualization under fluoroscopy or other visualization techniques to ensure a proper orientation, position, and placement of the cannula 360 relative to a target nerve and/or other tissues, structures, etc. It also will be understood that at least some conductive portions of cannula 360, needle 210 will be visualized under fluoroscopy or other visualization techniques to further aid ensuring proper placement, orientation, and/or position of those respective elements.

As shown in the sectional view of FIG. 6B, cannula 360 defines a lumen 370 that extends throughout body portion 366. In general terms, cannula 360 is a generally tubular structure with electrically conductive properties. Accordingly, as shown in FIG. 6B, in one aspect, body portion 366 has a dielectric or insulative coating 367 on its outer surface while distal tip 364 of cannula 360 omits a dielectric coating.

In one embodiment, distal tip 364 includes an end opening 390 sized and shaped to facilitate passage of a stimulation lead therethrough. Moreover, curved distal portion 372 is formed of a generally resilient, flexible material. Accordingly, upon slidably advancing cannula body 366 over a pre-placed site locator tool 200, as illustrated in FIGS. 4 and 7A, curved distal portion 372 assumes a generally straight shape to aid its insertion percutaneously through skin 402 and tissues 404, 405 at an angle generally perpendicular to the hypoglossal nerve, as shown in FIG. 7B. In addition, in this position, the proximal portion and/or handle 362 of tool 350 remains external to skin surface 402. It will be understood that in some embodiments, in the absence of site locator tool 200, a stiffener or stylet, as known to those skilled in the art, can be used to maintain the cannula body 366 in a straight configuration during its insertion percutaneously. One generally example of such stylets is described and illustrated in Buckberg U.S. Pat. No. 5,226,427, which is hereby incorporated by reference in its entirety.

In its straightened shape, cannula 310 has a shape substantially similar to that shown for tool 380 that is later described in association with FIG. 6C. Referring again to FIG. 6A, once the distal tip 364 is located at a desired depth, the locator tool 200 (or other stiffener) is removed causing the curved distal portion 372 to relax and resume its generally curved shape, as shown in FIG. 7C. This relaxation, in turn, orients distal end opening 378 to be generally parallel to the hypoglossal nerve 410 as shown in FIG. 7C, thereby assuming a position suitable to direct a stimulation lead to be slidably advanced along the hypoglossal nerve to a desired stimulation site. In some embodiments, upon such relaxation, the distal end opening 378 is oriented at a generally obtuse angle relative to the generally straight proximal portion of the cannula 310.

In some embodiments, as will be understood by those skilled in the art, when identifying the optimal stimulation site (A) from among multiple potential sites (e.g. A, B, C, etc.), the site locator tool 200 would also be used to identify a corresponding entry point (e.g., D, E, F, G, etc.) of the lead introduction tool that is distal or proximal to the optimal stimulation site (e.g., A), as illustrated in FIGS. 7A-7E. In one embodiment, the spacing (along an axis generally parallel to the hypoglossal nerve) between the entry point at the skin surface (e.g., E) and the optimal stimulation site (A) on the hypoglossal nerve is substantially equal to the distance (D1) that distal end opening 378 extends from the generally perpendicular (relative to the hypoglossal nerve) orientation of cannula body portion 366 when inserted.

In another embodiment, the spacing between the skin entry point and the optimal stimulation site is configured to further account for the length (represented by D2 in FIG. 6A) of the stimulation lead (including the electrode portion as represented by dashed lines 395) that would extend out of end opening 378 to deliver the electrode portion of the stimulation lead at the target stimulation site. This arrangement further insures that the final placement of the electrode portion of the stimulation lead accurately corresponds to the previously identified optimal or target stimulation site (e.g. A in FIGS. 7A-7E). However, it will be further understood that in some embodiments, the distal end of the stimulation lead is positioned to extend beyond the target stimulation site marked at distance D2 to ensure that the target stimulation site remains generally centered along the length of the electrode portion (e.g., electrode array 442 of portion 440 as later described in relation to FIG. 8A-8C) of the stimulation lead. In such embodiments, the distance D2 corresponds to a length no more than a length of the electrode portion and likely less than (e.g. about one-quarter, one-half, or three-quarters) a length of the electrode portion (e.g. electrode array 442 of portion 440 in FIGS. 8A-8C).

Accordingly, in this embodiment the total spacing (along an axis generally parallel to a longitudinal axis of the hypoglossal nerve in this region) between the skin entry point and the optimal stimulation site would be the combination of the distances D1 and D2. With this in mind, in one embodiment, after the optimal stimulation site (e.g. A from among A, B, C, etc.) is identified via the site locator tool 200, the site locator tool 200 is used to trace the path of the hypoglossal nerve (or other suitable anatomical landmark) to identify a skin entry point (e.g. E in FIG. 7A-7B) for the lead introduction tool 350 that spaced apart from the optimal stimulation site (e.g. A in FIGS. 7A-7B) by a distance of D1 plus D2.

In one aspect, tracking these distances D1 and D2 greatly enhances the introduction of the stimulation lead to arrive at the optimal stimulation site because of the relative absence of significant anatomical structures (e.g., bone canals, protuberances, etc.) in the region of the hypoglossal nerve that is to be stimulated.

In another embodiment, a lead introduction tool 380 (shown in FIG. 6A) includes substantially the same features and attributes as lead introduction tool 350 of FIGS. 6A-6B, except for including a straight distal portion 382 with a side opening 390 instead of the curved distal portion 372 and end opening 378 shown in FIG. 6A. Accordingly, in this embodiment, straight distal portion 382 includes the side opening 390 sized and shaped to facilitate passage of a distal portion of a stimulation lead therethrough. In one aspect, opening 390 is configured as a side-directed, non-coring opening for lumen 370. With this arrangement, upon insertion percutaneously, the cannula body 360 of tool 380 is oriented generally perpendicular relative to the skin and relative to the hypoglossal nerve, with the distal side opening 390 enabling a stimulation lead to exit cannula body 360 in a path extending at a generally obtuse angle relative to the orientation of body 360 (as it percutaneously extends through a skin surface and tissues) and generally parallel to the hypoglossal nerve to be advanced generally parallel to the hypoglossal nerve.

When using lead introduction tool 380, the distance D1 shown in FIG. 6A and FIGS. 7C-7E is generally not tracked because of the straight shape of distal portion 382 (including tip 384) and because the lead introduction tool 380 is oriented generally perpendicular to the hypoglossal nerve over the optimal stimulation site. However, in one aspect, one can optionally account for the length of the electrode portion of a stimulation lead as it would extend generally outward and away from the distal tip 384 through opening 390 (and generally perpendicular to a longitudinal axis of the cannula body 360). Accordingly, in the embodiment of lead introduction tool 380, in addition to identifying the optimal stimulation site (e.g. A in FIGS. 7A-7E) with the site locator tool 200, the operator would also identify a skin entry point (e.g. G in FIG. 7C) that is spaced by the distance D2 from the optimal stimulation site. The distance D2 generally corresponds to the length of the stimulation lead (including the electrode portion) that would extend out of distal side opening 390 to deliver the electrode portion of the stimulation lead at the target stimulation site. In this way, the operator insures that the electrode portion of the stimulation lead is accurately delivered to the identified target stimulation site (e.g. A). As noted previously, the distance D2 would have a length no more than, and likely less than, a length of the electrode portion (such as electrode array 442 in FIG. 8B) to ensure centering the electrode portion relative to the target stimulation site.

In some embodiments, the stimulation lead (e.g., stimulation lead 430 as will be described in association with at least FIGS. 8A-8E) is configured to be cooperable with a removably attachable stylet to facilitate advancing the stimulation lead through cannula 380 and through the tissue surrounding the target stimulation site. In particular, as the distal portion of the stimulation lead exits the distal side opening 410, the distal portion 436 will have to be advanced via tunneling through the surrounding tissue. With this in mind, the stylet will provide rigidity as the stimulation lead is tunneled to the target stimulation site and once the stimulation lead is properly positioned, the stylet is removed from its connection to the stimulation lead. Moreover, in some embodiments, this stylet is also used to selectively deploy an anchoring mechanism associated with the electrode portion of the stimulation lead.

In some embodiments, the cannula of lead introduction tool 350 or 380 is generally non-conductive and the conductive elements of the site locator tool 200 and/or of the stiffener are used as an electrically conductive pathway to confirm the location of the target stimulation site and/or the location of the skin entry point spaced from the target stimulation site.

In some embodiments, other types of introducing mechanisms are used to establish a percutaneous access pathway for a stimulation lead. For example, one introducing mechanism includes a guide wire and a needle having a cannula and a stylet. With this arrangement, the needle cannula is percutaneously inserted to establish a percutaneous pathway with aid from the stylet to steer, guide, and/or stiffen the needle cannula. After a path is established by the combination of the cannula and stylet, the stylet is removed. With the cannula still in place, a guide wire is inserted into a proximal portion of the cannula and advanced through the cannula until a distal portion of the guide wire is adjacent the target stimulation site. Next, with the guide wire still in place, the cannula portion of the needle is removed proximally over the guide wire, leaving just the guide wire in place. Using known techniques, a stimulation lead is releasably coupled to the guide wire and advanced, via the guide wire, through the established percutaneous access pathway until an electrode portion of the stimulation lead is adjacent the target stimulation site. With the stimulation lead remaining in place, the guide wire is then removed. Finally, the stimulation lead is anchored to maintain the electrode portion in an electrically coupled relationship with the target stimulation site of the nerve.

While various different shapes and forms of leads can be used in the methods and systems of the present disclosure, FIGS. 8A-8C illustrate one exemplary embodiment of a stimulation lead 430 is that is configured to be deployed percutaneously. In one embodiment, the stimulation lead 430 is delivered via the tools 200, 350, 380 (as previously described in association with FIGS. 4-7) while in other embodiments, the stimulation lead 430 is delivered via other minimally invasive delivery techniques. Various aspects of the delivery of stimulation lead 430 will be described herein in further detail.

As shown in FIGS. 8A-8C, stimulation lead 430 includes a front side 432 and a back side 434 with the lead 430 extending between a distal portion 436 and a proximal portion 438.

At distal portion 436, the front side 432 supports an electrode portion 440 including a first array 442 of electrodes 444. In general terms, substantially the entire length of the electrode portion 440 comprises a generally flat surface and when the back side 434 also forms a generally flat surface, then the entire distal portion 436 defining the electrode portion 440 comprises a generally flat or planar member (with the exception of the to-be-described protrusions 464 on back side 434).

This generally flat or planar configuration of distal portion 436 (including stimulation electrode portion 440) provides a low profile topography, thereby facilitating its advancement through the tissue surrounding the hypoglossal nerve. In addition, by having at least a generally flat surface of the front side 432 of distal portion 436, a much closer and effective interface between the stimulation electrode portion 440 and the surface of the hypoglossal nerve can be achieved. However, in some other embodiments, the front side 432 of the distal portion 436 is not generally flat, but has at least some curved portion or undulating portion. In one example, as illustrated in FIG. 8F, the curved portion of the front side 432 of the distal portion 436 forms a generally concave shape configured to accentuate the extent to which the electrode portion 440 reciprocally conforms to the generally arcuate shape of the outer surface of the hypoglossal nerve. In another example, as illustrated in FIG. 8G, the front side 432 of the distal portion 436 forms a generally convex shape. In one aspect, this generally convex shape is configured to accentuate slidable passage of the distal portion through the tissue surrounding the hypoglossal nerve to arrive at the optimal stimulation site Likewise, in some embodiments, the back side 434 of the distal portion 436 is not generally flat, but has at least some curved portion which can be concave or convex. In one aspect, a generally convex shape on the back side 436 is configured to accentuate slidable passage of the distal portion through the tissue surrounding the hypoglossal nerve to arrive at the target stimulation site.

In another aspect, because the front side 432 carries electrode portion 440, the back side 434 of the distal portion 436 is generally made or coated with an electrically insulative material. With this arrangement, back side 434 effectively acts as a shield to prevent the stimulation signal from affecting the sensory nerves and skin overlying the stimulation site.

In another aspect, at proximal portion 438 of stimulation lead 430, a second array 450 of electrodes 452 is formed on both the front side 432 and the back side 434 of stimulation lead 430. The first array 442 of electrodes 444 are electrically connected to the second array 450 of electrodes 452 with the second array 450 of electrodes 452 configured to provide electrical connection to the IPG (55 in FIG. 1 or 109 in FIG. 2). Via control from the IPG 55, each electrode 444 of stimulation electrode portion 440 is independently programmable to apply a stimulation signal that has a selectively controllable polarity, amplitude, frequency, pulse width, and/or duration.

In one embodiment, the first array 442 of electrodes 444 includes a lateral component (i.e., extending along a width W1) or a longitudinal component (i.e., extending along a length L1) of at least three electrodes in a guarded cathode electrode polarity arrangement. This guarded cathode electrode polarity arrangement hyperpolarizes tissues near the hypoglossal nerve while providing for complete depolarization of the volume of the hypoglossal nerve adjacent the electrode portion 440 of the stimulation lead 430. However, as shown in FIG. 8B, in some embodiments, the first array 442 includes a multitude of electrodes 444 (substantially greater than three) extending along the width and along the length of the electrode portion 440. This arrangement permits selection of different combinations of electrodes 444 from among the first array 442, thereby optimizing the stimulation of the hypoglossal nerve via an optimal combination of electrodes 444 within the first array 442. Moreover, in some embodiments, one or more of the electrodes 444 are varied in shape and/or pitch, or varied by staggering of the rows of electrodes 444.

In some embodiments, with the assumption that a diameter of the target nerve in the region of the target stimulation site is about 3 millimeters, the electrode portion 440 will have a width (W1 in FIG. 8B) of at least about 5 millimeters. Accordingly, in these embodiments, the width (W1) of the electrode portion 440 is at least substantially equal to or substantially greater than the diameter of the target nerve in the region of the target stimulation site. This relationship insures that the electrical stimulation signal (for treating sleep apnea) will affect the full cross-section of the nerve so that substantially all the axons of the target nerve will potentially be activated (depending upon the parameters of the applied stimulation signal).

A body portion 437 extends between the electrode portion 440 (at the distal portion 436) and the proximal portion 438. With the exception of electrodes 444, the body portion 437 is a generally insulative member devoid of electrodes on the front side 432 and back side 434. It is understood, of course, that wires extend through an interior of the body portion 437 to connect electrodes 444 to the IPG (55 in FIG. 1 or 109 in FIG. 2). In general terms, the body portion 437 has a length sufficient to extend from the electrode portion 440 to the IPG 55 (FIG. 1).

In some embodiments, the distal portion 436 of stimulation lead 430 includes an anchoring mechanism 462 located on back side 434, i.e. on an opposite side relative to the stimulation electrode portion 440. In one aspect, the anchoring mechanism 462 provides a cuff-less arrangement to secure the electrode portion 440 in close proximity to the nerve with the anchoring mechanism being disposed on an opposite side of the electrode portion 440 so that the anchoring mechanism 462 faces away from the nerve. This arrangement secures the electrode portion independently of the nerve and in a desired position relative to the nerve without placing any pressure or other mechanical effects on the nerve that might otherwise be used to secure an electrode relative to a nerve.

In one aspect, the anchoring mechanism 462 includes at least one array of protrusions 464. In one embodiment, the protrusions 464 are flaps formed of a resilient material while in other embodiments, the protrusions 464 are barbs, prongs, or other anchoring components. In some of these embodiments, the protrusions are sized and shaped to induce fibrotic growth at and near the protrusions to cause further anchoring of the distal portion 436 of the stimulation lead 430. In one aspect, within about one month, the protrusions 464 become ingrown with fibrotic tissue. Accordingly, while the protrusions 464 act to provide some long-term stability to the position of stimulation lead 430 within the body, one purpose of the protrusions 464 is to provide such stability for at least about one month, which generally corresponds to the amount of time for fibrotic tissue growth to effect a more permanent, long term stabilization of electrode portion 440 at the target site within the body.

In one aspect, the protrusions 464 extend generally outward at an angle (e.g., 30, 45, 60 degrees) from a surface of the back side 434 of the distal portion 436 of the stimulation lead 430. As shown in FIGS. 8A and 8B, in some embodiments, at least one pair of the protrusions 464 are provided in a divergent orientation which enhances the stability of the stimulation lead 430 by reducing the likelihood of the stimulation lead 430 from migrating away from its placed location. In particular, once implanted, the divergent orientation of the protrusions 464 enhance maintaining the electrode portion 440 of the stimulation lead 430 in its target location regardless of the direction of applied forces on the stimulation lead. In one aspect, the protrusions 464 have a length and width configured to engage or integrate with the tissues surrounding the hypoglossal nerve. However, in another aspect, the protrusions 464 form a generally tab-like structure made of a flexible polymer that can collapse upon application of a sufficiently high force, thereby enabling adjustment of the position of the electrode portion 440 of the stimulation lead 430 and/or removal of the stimulation lead 430.

In some embodiments, the protrusions 464 are sized and shaped to facilitate their disengagement from the surrounding tissues (via the use of a tool) to enable removal of the electrode portion 440 of the stimulation lead 430 from its implanted location adjacent the hypoglossal nerve. Such removal would take place in the event that a trial treatment plan was ineffective or in the event that the stimulation lead 430 was malfunctioning.

However, in the event that only some of the electrodes 444 were malfunctioning, the stimulation lead 430 need not be removed because the IPG 55 of FIG. 1 (or IPG 109 in FIG. 2) can be used to activate a different set of electrodes 444 within the first array 442 to produce a new combination of electrodes 444 arranged to apply a therapeutic regimen for treating sleep apnea. Moreover, an adjustment of the stimulation parameters (e.g., amplitude, pulse width, frequency, duration, and electrode polarity) via the IPG 55, 109 can compensate for the different position of the electrodes in the new combination of activated electrodes 444 for applying the stimulation signal. In this embodiment, the many varied positions of the electrodes 444 both along the length of the distal portion 436 of the electrode portion 440 of the lead 430 and transversely across the distal portion 436 enables precise activation of selective groups of electrodes 444 (at their various spaced apart locations) to produce an effective stimulation signal. Likewise, in the event that some inadvertent migration of the stimulation lead 430 occurs distally or proximally relative to the optimal stimulation site after the stimulation lead 430 has been considered to be properly placed, then the IPG 55 (or IPG 109 in FIG. 2) is used to activate a different set of electrodes 444 of the first array 442 to achieve a stimulation signal that compensates for the migration to maintain a proper stimulation signal at the target stimulation site.

The stimulation lead 430 is configured to balance various parameters including optimal electrode orientation, patient comfort, anchor strength, preventing migration of the lead, and providing for removability of the lead, as well as facilitating subcutaneous tunneling of the stimulation lead 430 to the site of the IPG. As such, this stimulation lead 430 provides several advantageous features, including providing for stimulation of the entire cross-sectional volume of the hypoglossal nerve volume in a manner comparable with cuff electrodes. Moreover, by facing the electrodes 444 away from the skin and by backing the electrodes 444 with an insulative layer (body portion 437), the stimulation lead 430 minimizes stimulation of nearby sensory nerves. In addition, by having an array 442 of multiple electrodes 444 that are independently programmable or controllable relative to each other via operation of IPG 55, the therapy can be adjusted in a non-invasive manner in the event that the stimulation lead 430 migrates from its original placement. In other words, the stimulation can be shifted from one combination of electrodes 444 in the array 442 to a different combination of electrodes 444 in the array 442 to account for the shift in the overall position of the electrode portion 440 of the stimulation lead 430 relative to the hypoglossal nerve. Of course, it will be understood that different combinations of electrodes 444 can be activated simply to achieve a different therapy regimen, even in the absence of migration or malfunction of electrode array 442.

Figure 7E:
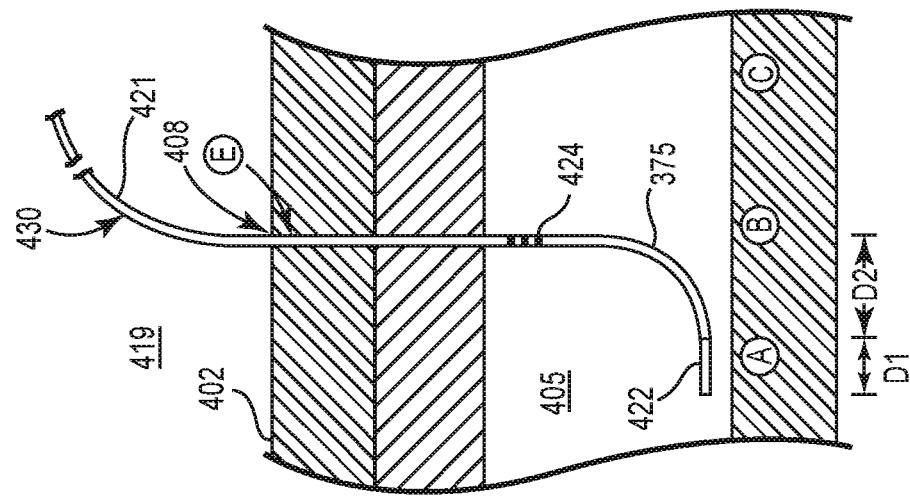
FIG. 7E is sectional view schematically illustrating a configuration of the stimulation lead upon removal of the introduction tool, according to an embodiment of the present disclosure.
Figure 7D:
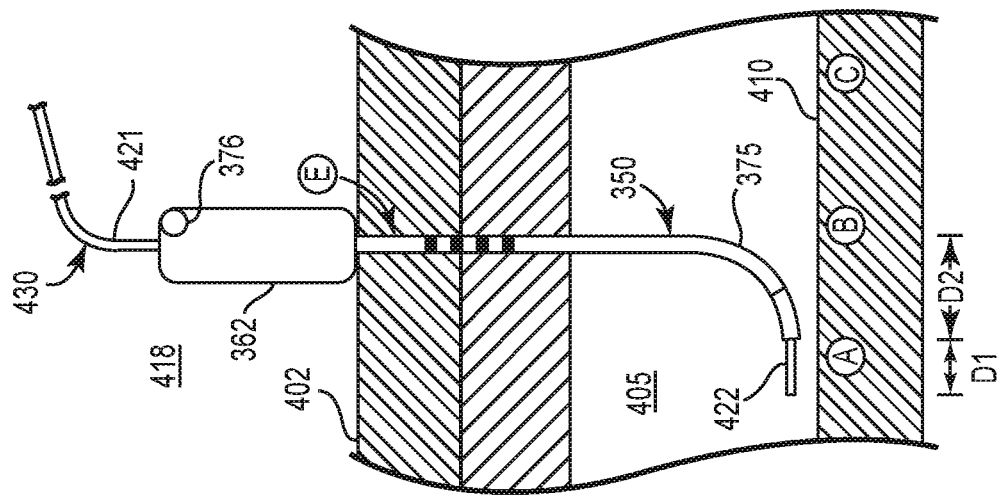
FIG. 7D is sectional view schematically illustrating a configuration upon insertion of a stimulation lead via the introduction tool, according to an embodiment of the present disclosure.

In use, the stimulation lead 430 is delivered percutaneously via feeding the distal portion 436 into a proximal portion 369 of the cannula 360 of lead introduction tool 350 or 380 and slidably advancing the distal portion 436 therethrough until the distal portion 436 of stimulation lead 430 exits the distal opening (390 or 410, respectively) of the lead introduction tool 350, 380 to be oriented generally parallel and closely adjacent to the hypoglossal nerve at a target stimulation site (e.g. A) with the electrode portion 440 facing toward the nerve and away from the skin (and underlying sensory nerves), as illustrated in FIG. 7D. Next, while maintaining the position of the distal portion 422 (e.g. electrode array 442 in FIG. 8B) stimulation lead 430, the tool 350 is withdrawn proximally from tissues 404, 405 to leave just stimulation lead 430 in place, as illustrated in FIG. 7E. From this configuration, the proximal portion 421 of stimulation lead 430 is tunneled and/or maneuvered subcutaneously to extend from the neck region to a pectoral region, to achieve a general configuration similar to that shown in FIG. 1 for lead 52.

In some embodiments, as shown in perspective view of FIG. 8D and the sectional view of FIG. 8E, a distal tip 364A of a lead introduction tool 350A includes a shell-like cover 480 protruding distally outward from the cannula body 360A and is configured with a wall 482 to control the deployment of the protrusions 464 of the anchoring mechanism 462 of stimulation lead 430. In particular, the wall 482 of cover 480 acts as a barrier to maintain the protrusions 464 in a collapsed position against or close too the back side 434 of the distal portion 436 of the stimulation lead 430 so that the protrusions 464 do not engage the surrounding tissue prior to proper positioning of the stimulation electrode portion 440 against the hypoglossal nerve. At the same time, the distal portion 364 continues to define an opening 365A generally opposite the cover 480 to enable exposing the electrode array 442 to the target nerve to allow testing or confirming positioning over the target stimulation site prior to deploying the anchor mechanism 462. In some embodiments, the cover 480 defines a half-circular cross-sectional shape having a diameter (D3) generally corresponding to a diameter of cannula 360. Once proper positioning of the stimulation electrode 440 has been achieved and upon proximally withdrawing the tool 350A, the cover 480 is withdrawn from its position over anchoring mechanism 462, thereby releasing protrusions to engage surrounding tissues. Likewise, in the event that the stimulation lead 430 must be removed, the cover 480 of the lead introduction tool 350 will force the collapse of the protrusions 464 (against the body of the distal portion 436 of the stimulation lead 430) as the distal portion 436 of the stimulation lead 430 is withdrawn proximally into the lead introduction tool 350A.

In another aspect, once implanted, a stimulation system for automatically treating obstructive sleep apnea will preferably remain in a stable position to endure the normal activities of the patient. For example, the neck of a patient moves through a wide range of motion through many different positions. To counteract the potential for a stimulation lead to move back and forth along the hypoglossal nerve (relative to a desired stimulation site), the anchoring mechanism 462 anchors the distal portion 436 of the stimulation lead 430 at the target stimulation site of the nerve. Accordingly, this anchoring mechanism insures that proper placement of the stimulation lead is maintained despite the dynamic motion and varying positions of the neck, which could otherwise cause inadvertent repositioning of the stimulation lead (relative to the target nerve) if the distal anchoring mechanisms were not present.

In addition, as previously noted, the anchoring mechanism 462 maintains this stable position without encircling the nerve (as a conventional cuff would) via an anchoring mechanism located on a directly opposite side of the distal portion 436 of the stimulation lead 430 with the anchoring mechanism 462 engaging the surrounding tissue instead of engaging the nerve. Nevertheless, to the extent that the electrode portion 440 of the distal portion 436 remains in close proximity or contact with the nerve, this relationship also contributes to the stability of the distal portion 436 because the anchoring mechanism 462 (on the opposite side from the electrode portion 440) is simultaneously securing the distal portion 436 in its desired position.

Figure 9:
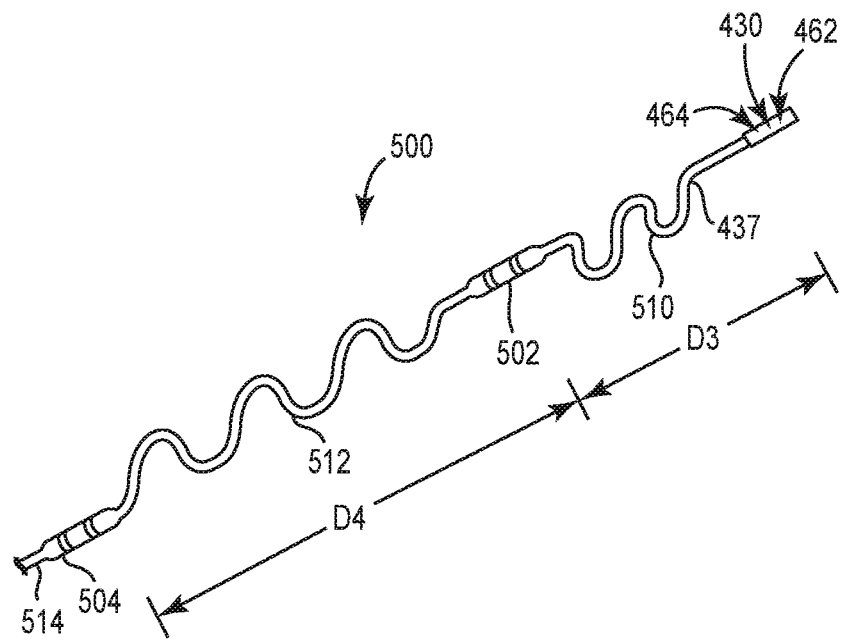
FIG. 9 is a perspective view of a stimulation lead including an anchoring system, according to an embodiment of the present disclosure.

Accordingly, in some embodiments, as shown in FIG. 9, a second anchoring mechanism 502 and/or third anchoring mechanism 504 is deployed to further stabilize the position of the stimulation lead 430 in addition to the first anchoring mechanism 462. As shown in FIG. 9, body portion 437 of stimulation lead 430 extends proximally from the electrode portion 440 and from the first anchoring mechanism 462 while the second anchoring mechanism 502 is positioned at a first distance (D3) away from the first anchoring mechanism 462. The third anchoring mechanism 504 is spaced proximally by a second distance (D4) from the second anchoring mechanism 502. As further shown in FIG. 9, a first region 510 (including portion 437) of simulation lead 430 extends between first anchoring mechanism 462 and second anchoring mechanism 502 while a second region 512 extends between second anchoring mechanism 502 and third anchoring mechanism 504. Finally, a third region 514 of lead 430 extends proximally from third anchoring mechanism 504 for passage toward the IPG (55 in FIG. 1 or 109 in FIG. 2).

In some embodiments, both the first region 510 and the second region 512 of the lead body 437 are pre-shaped into a serpentine or S-shaped configuration prior to deployment. In this pre-shaped configuration, first region 510 has a first length (D3) while second region 512 has a second length (D4). Once deployed via tunneling subcutaneously in a pathway proximally from the stimulation site, the S-shaped first and second regions 510, 512 provide strain relief mechanisms that act in concert with the first, second, and third anchoring mechanisms 462, 502, 504 to stabilize the position of the stimulation lead 430 while compensating for movements of the body as described above.

Figure 10:
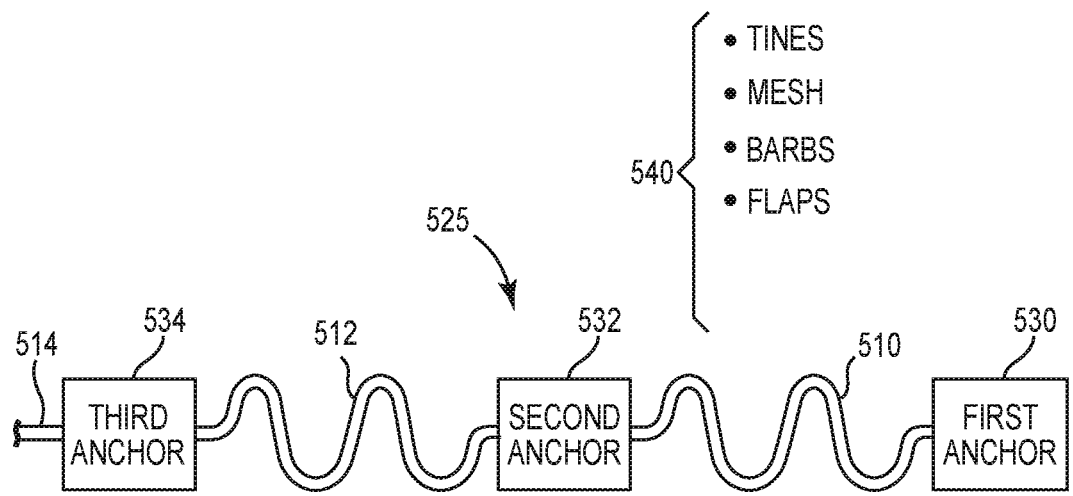
FIG. 10 is a perspective view of an alternate anchoring system, according to an embodiment of the present disclosure.

FIG. 10 is a side plan view of a stimulation lead including a dynamic anchoring system 525, according to an embodiment of the present disclosure. As shown in FIG. 10, system 525 includes a first anchor 530, second anchor 532, and a third anchor 534 with portions 510 and 512 of a stimulation lead interposed between the respective anchors. In one embodiment, one, two, or three of the anchors 530, 532, 534 include a biomediating mechanism, that is, a mechanism to induce fibrotic growth in the surrounding tissue at which the respective anchor is located and thereby further anchor the distal portion of a stimulation lead. As shown at 540 in FIG. 10, the anchors 530-534 comprise one or more of tines, mesh (e.g. Dacron mesh), barbs, flaps, and the like that are configured to mechanically engage the surrounding tissue.

In addition, in some embodiments, one or more of the anchors 530, 532, 534 are configured to provide a surface sized or treated (coated) to induce fibrotic growth to further secure the anchor. The "biomediating" anchors are particularly advantageous in a method of percutaneous delivery because the anchors do not require suturing, and therefore, regions 514, 512, and 510 of the stimulation lead can be tunneled toward the IPG 55 in FIG. 1 (or IPG 109 FIG. 2) without having to apply sutures when the anchors 530, 532, 534 arrive at their intended positions. However, it is understood that in some embodiments, minimally invasive suturing techniques can be applied as desired to further secure the respective anchors in place (during the initial period of fibrotic growth) to supplement the securing strength of the mechanical component (e.g., barbs, flaps, etc.) of the respective anchors.

FIGS. 11-14 schematically illustrate a method 550 of percutaneously delivering an electrode portion of a stimulation lead to a target nerve, according to an embodiment of the present disclosure. In viewing the FIGS. 11-14, it will be understood that sizes and/or relative spacing of various components of the anatomy (e.g., a size or width of incision, nerves, muscles, skin layer, etc.) and/or components of the tools (e.g., barbs, rods, etc.) have been exaggerated for illustrative clarity to highlight application of the tool. This method achieves placement of the electrode portion without the generally disruptive, and more time consuming, conventional cut-down implantation procedure (which would typically include a full dissection around the target nerve). Moreover, it is understood that prior to deployment of method 550, one or more optimal stimulation sites on the hypoglossal nerve have been identified via a site locator tool (e.g. site locator tool 200) or via other tools. It is also understood that one or more surgical navigation techniques are used to: (1) employ the site locator tool to identify the optimal stimulation site; (2) make an incision to provide a skin entry point generally over the optimal stimulation site; and (3) guide the distal portion of an introduction tool or implantation instrument to that optimal stimulation site.

Figure 12:
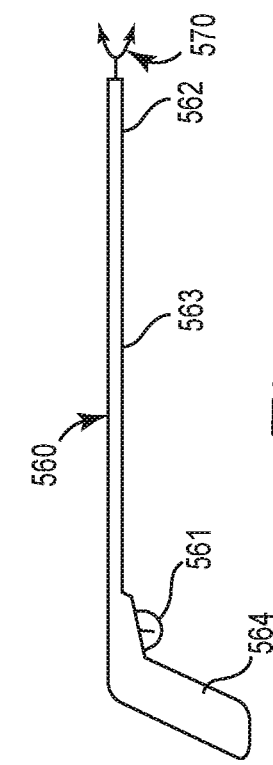
FIG. 12 is a side plan view of an introduction tool employed in the method associated with FIG. 11, according to an embodiment of the present disclosure.
Figure 11:
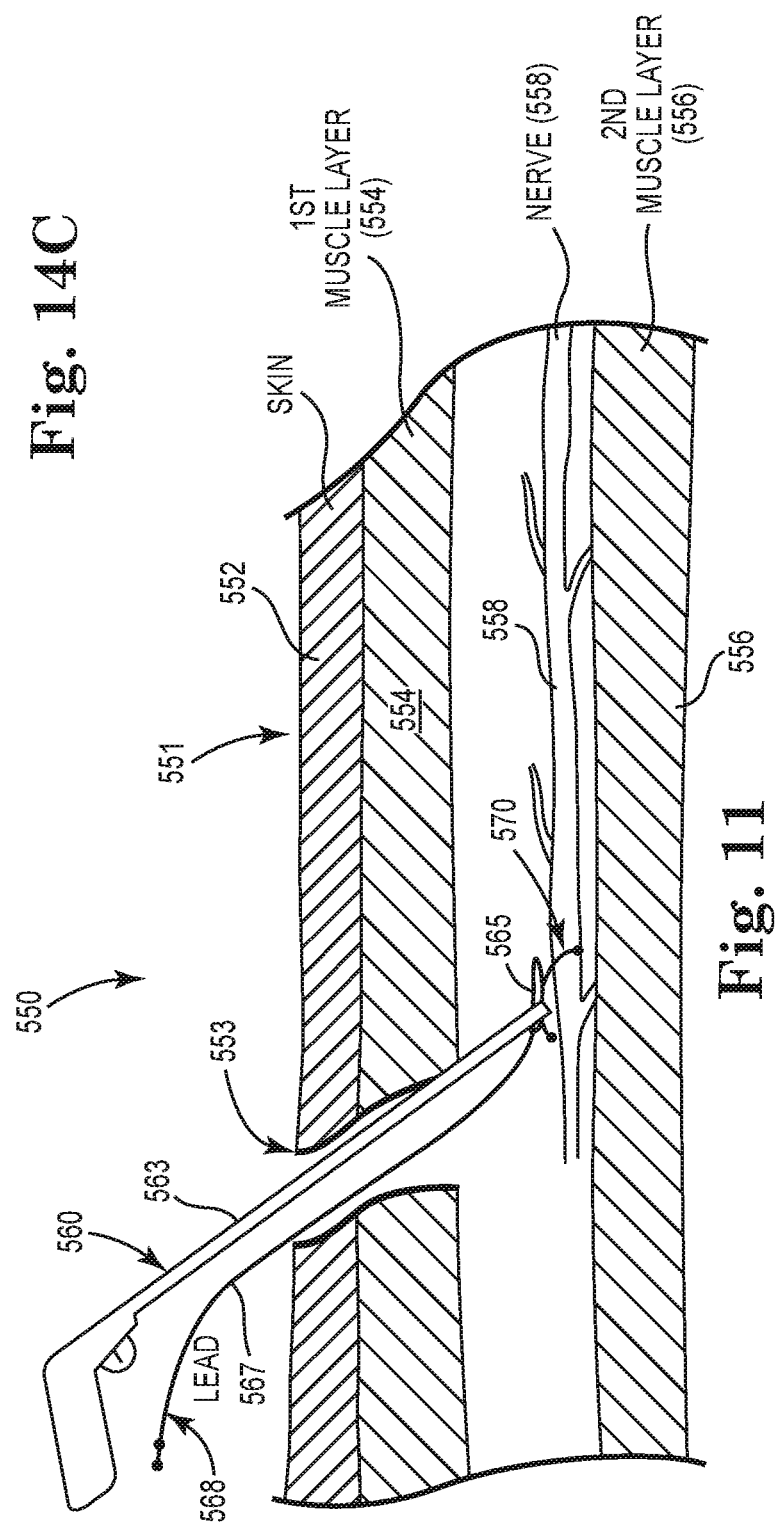
FIG. 11 is a sectional view schematically illustrating a method of percutaneous delivery of a stimulation lead, according to an embodiment of the present disclosure.
Figure 14A:
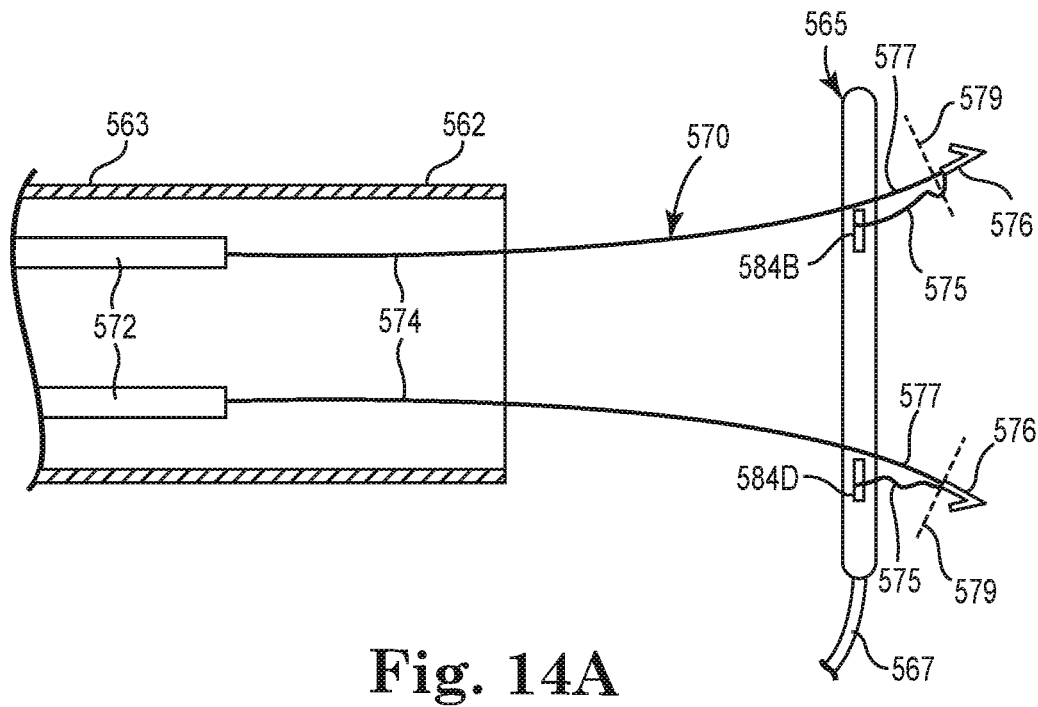
FIG. 14A is an enlarged sectional view schematically illustrating a selectively deployable anchoring mechanism of the introduction tool of FIGS. 11-12, according to an embodiment of the present disclosure.

As shown in FIG. 11, method 550 includes making an incision 553 through the skin 552 and through first muscle layer 554 to provide access to the previously identified optimal stimulation site at target nerve 558, such as the hypoglossal nerve. The incision is relatively small, such as 2 centimeters wide, so that the access to the nerve 558 is considered minimally invasive. Next, via use of an implantation instrument 560, an electrode portion 565 of a stimulation lead 568 is inserted through the incision 553 and guided to the nerve 558. As shown in FIG. 12, the implantation instrument 560 includes a distal tip 562 from which a selectively deployable, engagement mechanism 570 protrudes and a barrel 563 extending proximally between a handle 564 and distal tip 562. The barrel 563 is configured to support deployment of the engagement mechanism 570. A trigger 561 mounted at handle 564 is connected to a proximal end of the engagement mechanism 570 and controls selective deployment of the engagement mechanism 570.

Figures 13, 14B:
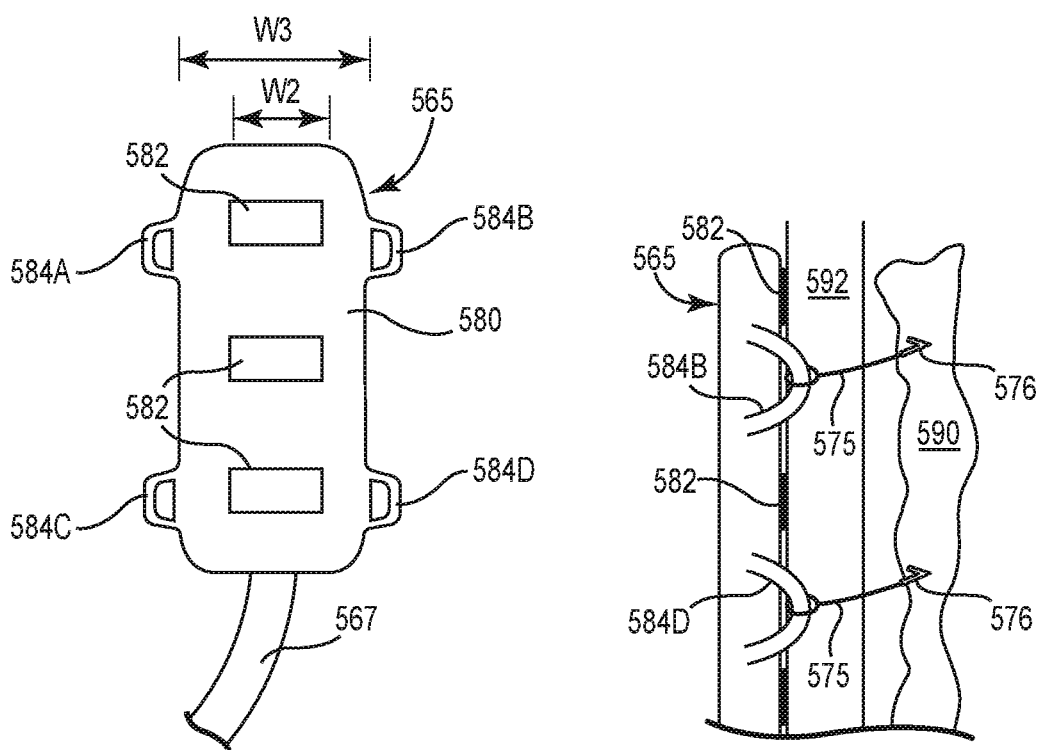
FIG. 13 is a bottom plan view of a distal electrode portion of a stimulation lead, according to an embodiment of the present disclosure.
FIG. 14B is an enlarged side view schematically illustrating the anchoring mechanism in a deployed state relative to the surrounding tissue, according to an embodiment of the present disclosure.

Moreover, in one embodiment, as shown in FIG. 13, the electrode portion 565 comprises an insulative carrier 580 supporting an array of spaced apart electrodes 582 aligned in series. The carrier 580 also includes an array of securing elements 584A, 584B, 584C, 584D extending outward from the sides and/or ends of the carrier 580 to facilitate securing the carrier 580 relative to the surrounding tissues adjacent the hypoglossal nerve. The securing elements 584A-584D can be loops or any other structure to which a suture or fastener is securable relative to the surrounding tissue. In this way, the electrodes 582 of the electrode portion 565 become secured relative to nerve 558 with the electrodes 582 facing the nerve 558. In one embodiment, the electrodes 582 are aligned with a longitudinal axis of the electrode portion 565 and/or of the stimulation lead supporting the electrode portion 565. As previously noted, the electrode portion 565 is implanted so that the electrodes 582 also face away from the skin 552 (with carrier 580 acting as a shield) to minimize stimulation of sensory nerves at or near the skin 552.

In one aspect, as shown in FIG. 13, the electrodes 582 have a width W2 (at least 3-5 millimeters) generally equal to or greater than a diameter of the target nerve (e.g., 3 millimeters) while carrier 580 has a width (W3) substantially greater than the width W2 of the electrodes 582 to insure shielding of the skin from the stimulation signal emitted from electrodes 582.

Referring again to FIG. 11, once the electrode portion 565 is properly positioned over the nerve 558, the implantation instrument 560 secures the electrode portion 565 in position relative to the nerve 558 via engagement mechanism 570. While the engagement mechanism 570 can take many different forms, in one embodiment shown in FIG. 14, the anchoring mechanism 570 protrudes from the distal portion 562 of barrel 563 of implantation instrument 560.

In particular, the anchoring mechanism 570 includes one or more small diameter rods 572 extending longitudinally within a conduit formed by barrel 563 with each rod 572 supporting a needle 574 configured to selectively extend distally from an end of each respective rod 572. In one embodiment, barrel 563 includes a generally hollow, elongate tubular member, and the rods 572 extend through a length of the barrel 563 while being longitudinally movable within the barrel 563.

Each needle 574 includes a barb 576 removably mounted at a distal end 575 of the needle 574. In one embodiment, barbs 576 are made from a stainless steel material or a plastic material while having a relatively small length and/or diameter (e.g., 1-3 millimeters) to avoid patient discomfort. In addition, a suture 575 includes a first end connected to the barb 576 and a second end connected to securing elements 584 of electrode portion 565 of the stimulation lead. In a pre-deployment state, the respective sutures 575 are in a relaxed state without tension. In one embodiment, needles 574 are formed of a metal, such as a Nitonol material.

Accordingly, with the electrode portion 565 positioned over an optimal stimulation site of the nerve 558, trigger 561 activates anchoring mechanism 570 to automatically cause the rods 572 to force the needles 574 to protrude distally outward and penetrate into surrounding tissues adjacent the nerve 558 and electrode portion 565, and then the trigger 561 is subsequently relaxed causing retraction of rods 572 and their respective needles 574. However, the barbs 576 remain fixed in the surrounding tissues because they detach from the needles 574 (at a point of detachment represented by dashed lines 579) as the needles 574 are retracted. At this point, the implantation instrument 560 is removed from the incision site, leaving the electrode portion 565 in place.

In one aspect, as the needles 574 are advanced to place the barbs 576 into the tissue the sutures 575 become under tension, and as the needles 574 are retracted into barrel 563 with the barbs 576 remaining in the tissue, the sutures 575 remain under tension which effectively exerts tension on the carrier 580 to urge electrodes 582 into pressing contact against the nerve. For example, as schematically illustrated in the side view of FIG. 14B, with barbs 576 deployed in tissue 590, securing elements 584B, 584D (and their respective sutures 575) are under tension, thereby urging electrode portion 565 (and particularly electrodes 582) against the nerve 592. This arrangement provides longitudinal stability to the secured position of the electrode portion 565 relative to the nerve. While not shown it is understood that the securing elements 584A, 584C on the opposite side of the electrode portion 565 also would be deployed via sutures 575 and barbs 576 so that all four securing elements 584A, 584B, 584C, 584D of electrode portion 565 are deployed. Accordingly, when secured under tension relative to the tissue 592 (via sutures 575 and barbs 576), securing elements 584A and 584C also provide longitudinal stability to the position of the electrode portion 565 relative to the nerve 590.

Moreover, in such an arrangement, securing element 584A and securing element 584B are positioned on opposite sides of the electrodes 582 to straddle the nerve 592, thereby insuring lateral stability of the electrode portion 565. Likewise, securing element 584C and securing element 584D are positioned on opposite sides of the electrodes 582 to straddle the nerve 592, thereby insuring lateral stability of the electrode portion 565.

Figure 14C:
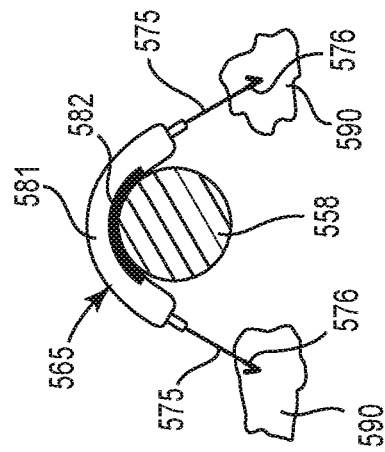
FIG. 14C is a sectional view schematically illustrating a distal electrode portion of a stimulation lead secured relative to a nerve via an anchoring mechanism, according to an embodiment of the present disclosure.

In some embodiments, as shown in FIG. 14B, the securing elements 584 are made of a flexible material to permit their bending toward the tissue to facilitate securing the barbs 576 and sutures 575 under tension. In these embodiments, the carrier 580 supporting the securing elements 584 can be either substantially rigid as shown in FIG. 14B or can be generally flexible as shown in FIG. 14C. In particular, as shown in the schematic sectional view of FIG. 14C, an electrode portion 565 includes a flexible carrier 581 supporting electrodes 582 with the carrier 581 configured to flexibly conform to the arcuate shape of the cross-section of the nerve 558. This arrangement insures close contact of the electrode 582 relative to the nerve 558 and accentuates the application of tension on sutures 575 when barbs 576 are anchored into the surrounding tissue 590. In another aspect, it will be clear from a consideration of both FIGS. 14B and 14C, the securing elements include a first array of barbs for deployment on one side of the electrode portion 565 and a second array of barbs for deployment on an opposite side of electrode portion 565.

After securing the electrode portion 565, the implantation instrument 560 is removed and the lead body 567 of the stimulation lead 568 is delivered subcutaneously, via a tunneling tool, from the anchored site of the electrode portion 565 to the IPG 55 (FIG. 1).

Various configurations of stimulation electrode portions of a stimulation lead are described and illustrated in association with the embodiments of FIGS. 15-27. These various stimulation electrode portions can be delivered percutaneously or via other suitable delivery techniques. In some embodiments, the electrode portions and/or supporting proximal portions of the stimulation lead are configured to have a minimal mechanical impact on the nerve and the surrounding tissues and/or are configured to be implanted via minimally invasive techniques.

FIGS. 15-17B schematically illustrate stimulation system including a bio-absorbable electrode portion 601 of a stimulation lead 600, according to an embodiment of the present disclosure. It is understood that prior to deployment of electrode portion 600, one or more optimal stimulation sites on the hypoglossal nerve have been identified via a site locator tool (e.g. site locator tool 200 shown in FIG. 3) or via other tools. It is also understood that one or more surgical navigation techniques are used to: (1) employ the site locator tool to identify the optimal stimulation site; and (2) place the electrode portion at that optimal stimulation site.

As shown in FIG. 15, stimulation lead 600 comprises an electrode portion 601 including cuff 602 and electrodes 610, as well as wires 612, anchor 614, and non-absorbable portion 620 of stimulation lead 600. In one embodiment, the cuff 602 comprises a generally elongate tubular member that carries electrodes 610 and is configured to wrap around nerve 625 in a releasably secured manner with a generally cylindrical shape, thereby maintaining electrodes 610 in close contact against nerve 625. A wire 612 extends proximally through the cuff 602 from each of the respective electrodes 610 and has a length extending further to anchor 614 and non-absorbable portion 620 so that the wires 612 are in electrical communication with IPG 55 (FIG. 1).

Figure 17A:
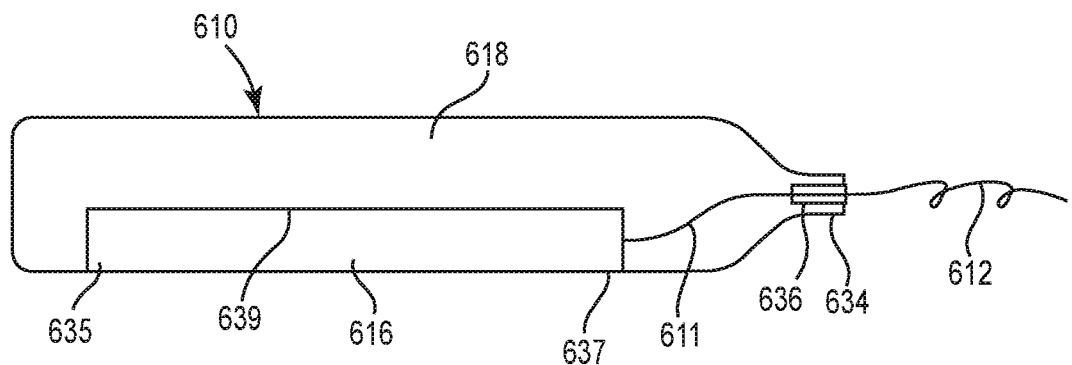
FIG. 17A is an enlarged side plan view of an electrode portion of the stimulation system of FIGS. 15-16, according to an embodiment of the present disclosure.

In some embodiments, as shown in FIG. 17A, each electrode 610 includes a conductive contact portion 616 and an electrically insulative cover 618. The electrically insulative cover 618 extends over the top portion 639 of the contact portion 616, extends beyond all four sides of contact portion 616, including sides 635, 637 viewable in FIG. 17A. At a proximal end 634 of the electrode 610, a strain relief member 636 connects wire 612 to contact portion 616 via wire 611. In one embodiment, electrodes 610 are embedded in the cuff 602 with bottom portion 638 exposed at inner surface of cuff 602. In some embodiments, electrodes 610 are aligned such that a longitudinal axis of each electrode 610 is generally perpendicular to a longitudinal axis of the cuff 602 and the respective electrode 610 are spaced apart from each other along a length of the cuff 610.

In one aspect, cuff 602 is made of a bio-absorbable material so that over a period of several weeks following the implantation of electrode portion 601, the cuff 602 is absorbed by the body, thereby leaving the electrodes 610 in their desired position relative to nerve 625. At the same time that the cuff 602 is being absorbed, tissue growth occurs at and around the wires 612 and occurs at and around the electrodes 610 as they become exposed from absorption of cuff 602. In some embodiments, wires 612 are arranged with several coiled portions 613 (highlighted in the enlarged caption in FIG. 15) to further induce fibrotic tissue growth at and around the wires 612 such that tissue growth at each coiled portion acts as a separate anchor.

Figure 17B:
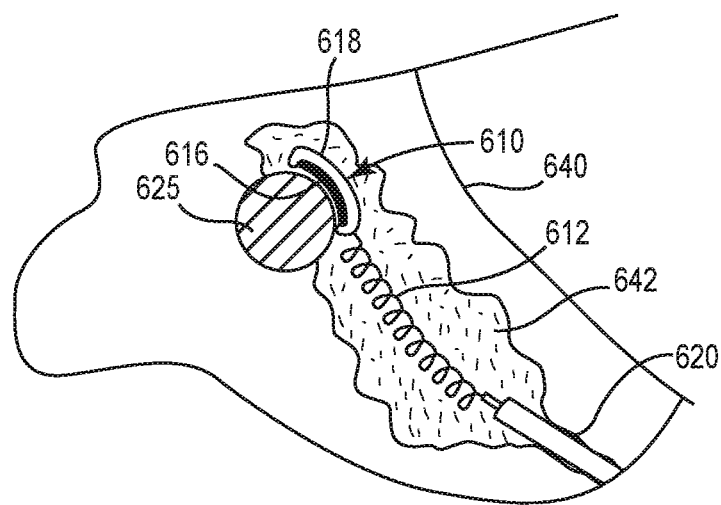
FIG. 17B is a sectional view as taken along lines 17B-17B of FIG. 16, according to an embodiment of the present disclosure.

After the absorption process for cuff 602 (and any other bio-absorbable components) is complete, the fibrotic tissue growth is sufficient to act as an anchoring mechanism to maintain the position of the electrodes 610 in their generally spaced apart relationship at the intended stimulation site and to secure the wires 612 to further maintain the position of electrodes 610. The resulting arrangement is illustrated in FIGS. 16 and FIG. 17B. In the sectional view of FIG. 17B, fibrotic tissue growth 642 surrounds the electrode 610 and wires 612 to mechanically secure the electrodes 610 in position over nerve 625 beneath skin/muscle portion 640. As further shown in FIG. 17B, insulative cover 618 protects each electrode 610 from the tissue growth 642. In one aspect, the insulative cover 618 covers a top portion and sides of each electrode 610 while a bottom portion of each electrode element 610 remains exposed to nerve 625. In some embodiments, the outer surface of insulative cover 618 includes a coating configured to induce the fibrotic tissue growth.

In one aspect, by employing a bio-absorbable cuff and inducing tissue growth to secure electrodes 610, this system provides minimal long-term impact at the implantation site.

In particular, the implanted, cuff-less set of electrodes 610 will be comfortable for the patient because of the absence of the relatively bulky size of a conventional cuff. This cuff-less arrangement also will be less likely to induce inadvertent mechanical effects on the target nerve (as compared to a conventional cuff electrode system), which can affect nerve function and comfort.

In some embodiments, anchor 614 is also made of bio-absorbable material and is absorbed over time within the body. Accordingly, tissue growth also would occur in this region to further secure wires 612 in place.

However, in some embodiments, as shown in FIGS. 15-16, the stimulation lead 600 includes a non-absorbable fastener 622 configured to maintain the separate wires 612 in a grouped arrangement. In one aspect, fastener 622 insures an orderly transition of the separate wires 622 to the permanent lead portion 620 that extends to the IPG 55 (FIG. 1). In another aspect, fastener 622 also provides strain relief to prevent inadvertent pulling of wires 612 on the target nerve. However, in other embodiments, this fastener 622 is omitted or is made of a bio-absorbable material.

FIGS. 18-21 schematically illustrate a bio-absorbable electrode portion 650 of a stimulation lead, according to an embodiment of the present disclosure. It is understood that prior to deployment of electrode portion 650, one or more optimal stimulation sites on the hypoglossal nerve have been identified via a site locator tool (e.g. site locator tool 200) or via other tools. It is also understood that one or more surgical navigation techniques are used to: (1) employ the site locator tool to identify the optimal stimulation site; and (2) place the electrode portion at that optimal stimulation site. Finally, it is also understood that the electrodes 660 of electrode portion 650 would be electrically connected via wires and a lead body to an IPG 55 (FIG. 1) and that this general arrangement is omitted in FIGS. 18-21 for illustrative clarity.

Figure 18:
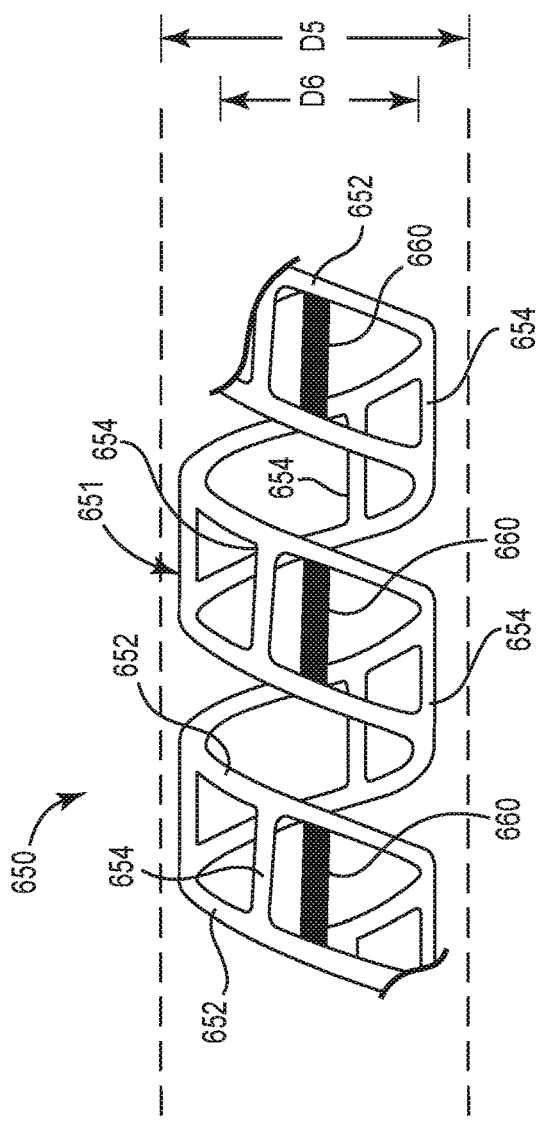
FIG. 18 is a side plan view of a bio-absorbable, stent-electrode stimulation lead, according to an embodiment of the present disclosure.
Figure 19:
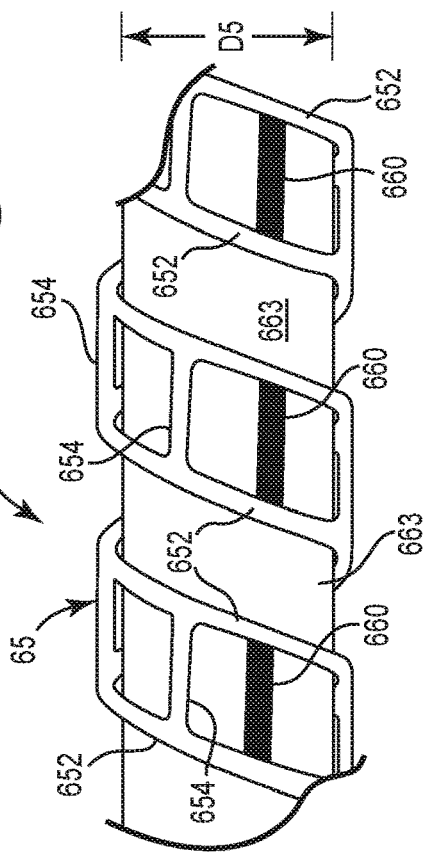
FIG. 19 is a side plan view schematically illustrating deployment of the stent-electrode stimulation lead of FIG. 18 relative to a nerve, according to an embodiment of the present disclosure.

FIGS. 18-19 are plan views of an electrode portion 650 of a stimulation lead in which the electrode portion 650 includes a generally flexible coil member 651 and electrodes 660. In general terms, the coil member 651 wraps around a nerve 663 and defines a stent-like insulative member that maintains electrodes 660 in close contact against nerve 663. However, unlike a conventional cardiovascular stent which is deployed within a blood vessel via expanding the stent outward against the wall of the blood vessel, the coil member 651 is configured to wrap around an outer surface of a nerve 663 in a self-sizing relationship and is not configured to expand radially when deployed in the desired position.

In some embodiments, the coil member 651 forms a generally helical shape and includes a pair of spaced apart rails 652 with numerous struts 654 extending between and interconnecting the rails 652. In one embodiment, the rails 652 and struts 654 are made of non-conductive materials. In one aspect, electrodes 660 are sized and shaped to extend between a pair of rails 652, as shown in FIGS. 18-19, in a manner similar to the struts 654. In one embodiment, the electrodes 660 are in general alignment with a longitudinal axis of the coil member 651. However, it will be understood that the coil member 651 is not strictly limited to the arrangement of rails 652 and struts 654 shown in FIGS. 18-19 because numerous variations and arrangements of struts can be used to form the helically shaped coil member.

As shown in its pre-deployment state in FIG. 18, coil member 651 has an inner diameter (D6) that is substantially less than a diameter (D5) of the target nerve 663 (see also FIG. 19). Accordingly, when coil member 651 is placed about the larger diameter nerve 663, the coil member 651 wraps about the nerve 663 in a self-sizing manner such that the inner diameter of the coil member 651 substantially matches the diameter of the target nerve 663, as shown in FIG. 19. To the extent that any spacing is shown between the coil member 651 and nerve 663 in FIG. 19, this spacing is provided for illustrative clarity to clearly define the components of the coil member 651 separately from nerve 663.

In some embodiments, the coil member 651 attracts tissue growth at rails 652 and struts 654 with the combination of the tissue growth and the rails 652 and struts 654 acting as an anchoring mechanism to maintain the electrodes 660 in close contact against nerve 663.

Figure 20:
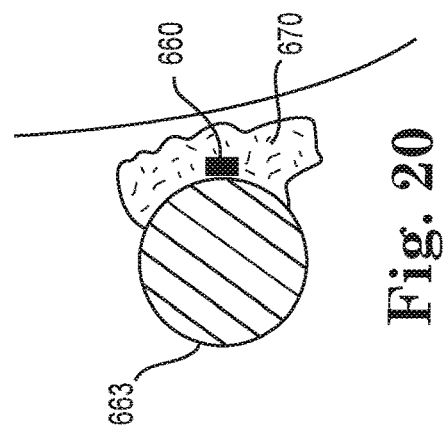
FIG. 20 is a sectional view schematically illustrating anchoring of an electrode against a nerve after absorption of the bio-absorbable stent portion of the stimulation lead, according to an embodiment of the present disclosure.
Figure 21:
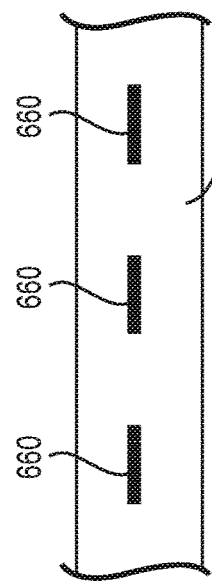
FIG. 21 is a side plan view schematically illustrating the electrodes of the stimulation lead against the target nerve after absorption of the bio-absorbable stent portion of the stimulation lead, according to an embodiment of the present disclosure.

In some other embodiments, the coil member 651 forms a bio-absorbable material so that after absorption of rails 652 and struts 654 takes place, electrodes 660 remain in close contact to nerve 663 with tissue growth 670 on and around the electrodes 660 holding the electrodes 660 in place relative to the nerve 663, as shown in FIGS. 20-21. The various components (struts and rails) of the coil member 651 form a latticework or frame configured to induce fibrotic tissue growth in a pattern generally matching the structure of the coil member 651 so that the induced tissue growth forms in a mechanically advantageous framework holding the electrodes 660 in place relative to the nerve 663. In one aspect, this framework of fibrotic growth forms a bio-cuff in which tissues produced within the body form a cuff to maintain the electrodes 610 in the desired position relative to the nerve.

It is understood that tissue growth also would occur at and around the wires (not shown) extending proximally from the electrodes 660 toward the IPG 55 (FIG. 1). It is further understood, that similar to previous embodiments, an outer portion of the electrode 660 (the portion that does not contact the nerve 663) would include an insulative cover to act as a barrier between the contact portion of the electrode 660 and the surrounding tissue.

Moreover, in one embodiment, each electrode 660 is connected to a respective one of an array of wires with each respective wire connected to, and extending to, a stimulation lead body configured for electrical communication with an IPG 55 (FIG. 1). In one embodiment, the array of wires includes substantially the same features and attributes as the array of wires 612, as previously described and illustrated in association with FIGS. 15-16.

Figure 22:
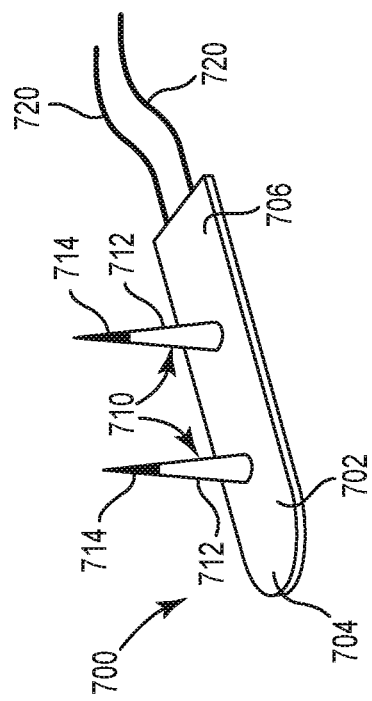
FIG. 22 is a perspective view schematically illustrating a bio-absorbable electrode portion of a stimulation lead, according to an embodiment of the present disclosure.
Figure 23:
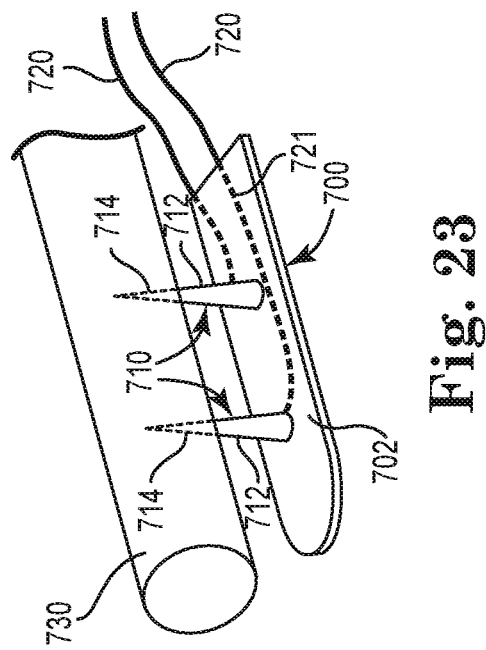
FIG. 23 is a perspective view schematically illustrating implanted electrodes of the stimulation lead of FIG. 22 prior to absorption, according to an embodiment of the present disclosure.
Figure 24:
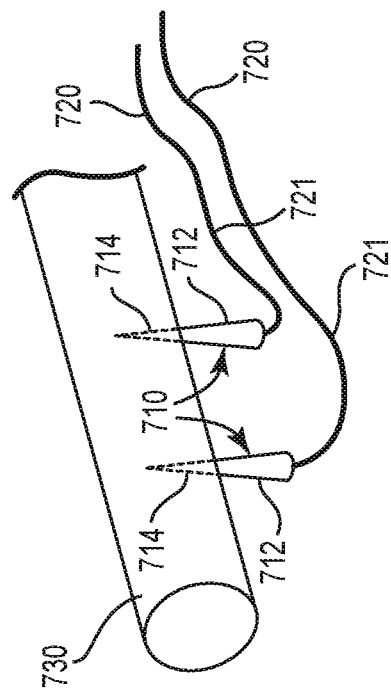
FIG. 24 is a perspective view schematically illustrating the implanted electrodes of the stimulation lead of FIG. 22 after absorption, according to an embodiment of the present disclosure.

FIGS. 22-24 schematically illustrate an electrode portion 700 of a stimulation lead, according to an embodiment of the present disclosure. It is understood that prior to deployment of electrode portion 700, one or more potential stimulation sites on the hypoglossal nerve have been identified via a site locator tool (e.g. site locator tool 200) or via other tools. It is also understood that one or more surgical navigation techniques are used to: (1) employ the site locator tool to identify the optimal stimulation site; and (2) place the electrode portion at that optimal stimulation site.

As shown in FIGS. 22-23, electrode portion 700 includes a carrier 702 supporting generally spike-shaped electrodes 710 that are spaced apart from each other along a length of the carrier 702. The carrier 702 includes a distal end 704 and a proximal end 706 while each electrode 710 forms a conductive member including an exposed distal tip 714 and an insulative covered base portion 712. While just two electrodes 710 are shown, it will be understood that in other embodiments, carrier 702 supports more than two electrodes 710. In one embodiment, the carrier 702 comprises a generally flat member having a first side and a second side (opposite the first side), with the electrodes 710 extending generally outward from the first side of the generally flat member.

In another aspect, for each electrode 710, a separate wire 720 extends through the carrier 704 (shown as dashed lines in FIG. 23) and is electrically connected to the base portion 712 of each respective electrode 710. It is further understood that the electrodes 710 are formed of ultra fine wires, as known to those skilled in the art, and that the electrodes 710 are shown in FIGS. 22-24 in an exaggerated, enlarged form strictly for illustrative purposes.

Once the electrode portion 700 is delivered to the intended stimulation site, pressure is applied to insert the distal tips 714 of the respective electrodes 710 into the nerve 730. Because of the small dimensions of the ultra fine wire forming each electrode 710, the electrodes 710 are maintained in this position via the tissue of the nerve effectively capturing the electrodes 710. With this arrangement, close contact of the electrodes 710 to the nerve 730 is insured, resulting in effective stimulation of the nerve 730.

In some embodiments, once the electrode portion 700 is secured in place, the electrode portion 700 attracts tissue growth (not shown) about carrier 702 and base portion 712 of needles 710 with the combination of the tissue growth and the carrier 702 and base portions 712 acting as an anchoring mechanism to maintain the electrode tips 714 in penetrating engagement (i.e. inserted engagement) relative to nerve 730.

In some other embodiments, the carrier 702 forms a bio-absorbable material so that carrier 702 is absorbed over time, leaving just electrodes 710 and wire portions 721, 720 in place at nerve 730, as shown in FIG. 24. As the absorption of carrier 702 occurs, electrodes 710 are held in inserted engagement relative to nerve 730 because of tissue growth (not shown) forming on and around the base portion 712 of electrodes 710 (as the carrier is absorbed) to hold the electrodes 710 in penetrating engagement relative to the nerve 730. It is understood that a similar tissue growth would occur at and around the wire portions 721 and 720 extending proximally from the electrodes 660 toward the IPG 55 (FIG. 1).

Figures 25, 26, 27, 28, 29:
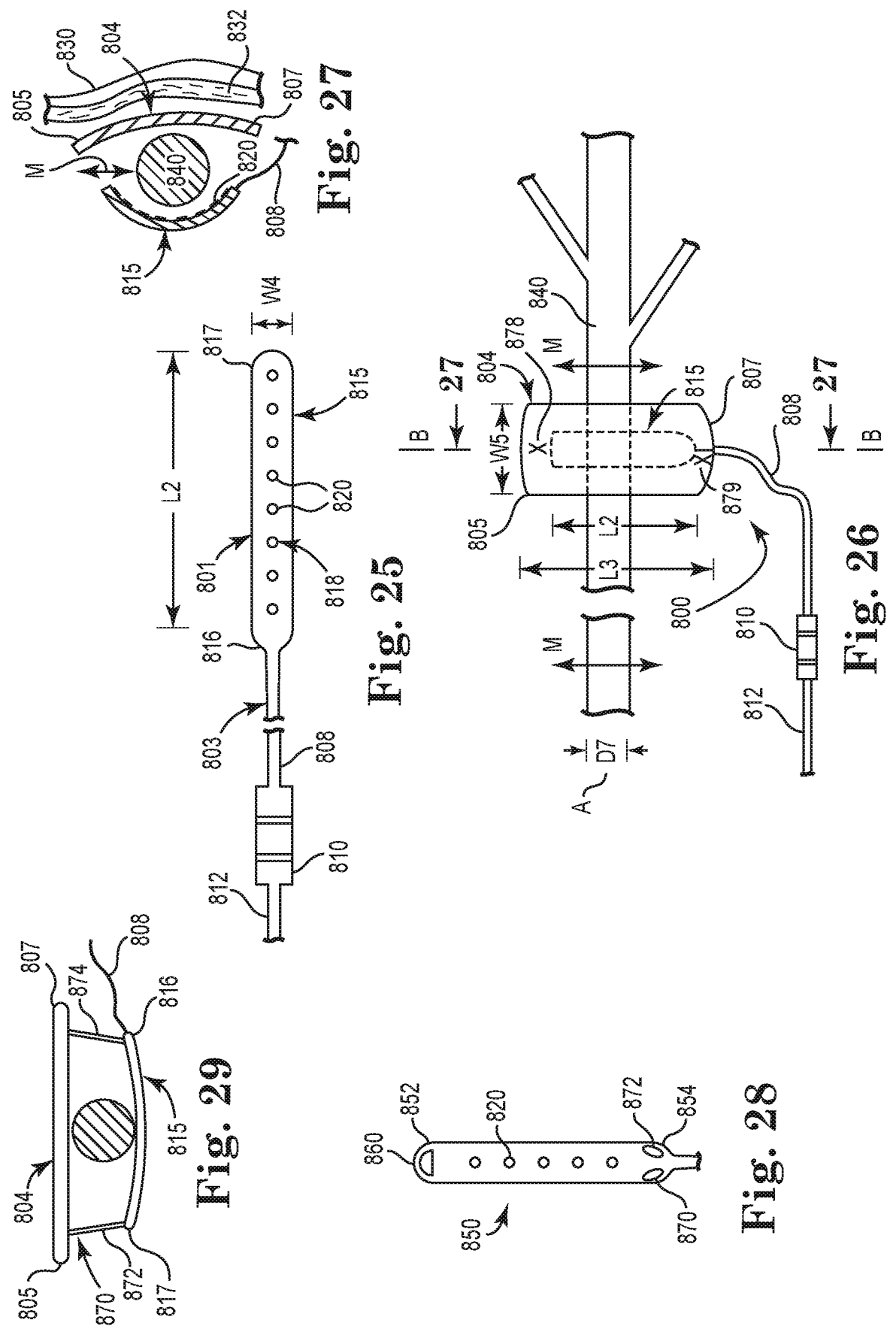

FIGS. 25-32 schematically illustrate stimulation system 800 and a method of implanting components of system 800, according to an embodiment of the present disclosure. As shown in FIGS. 25-27, the stimulation system 800 includes at least an electrode portion 801 of a stimulation lead 802 and a shield 804. It is understood that prior to deployment of electrode portion 801, one or more optimal stimulation sites on the hypoglossal nerve have been identified via a site locator tool (e.g. site locator tool 200 shown in FIG. 1) or via other tools. It is also understood that one or more surgical navigation techniques are used to: (1) employ the site locator tool to identify the optimal stimulation site; and (2) place the electrode portion at that optimal stimulation site.

As shown in FIG. 25, stimulation lead 803 includes electrode portion 801 and lead body 808 with the electrode portion 801 including a generally elongate carrier body extending between a distal end 817 and a proximal end 816, and an electrode strip 815, which includes an array 818 of electrodes 820 spaced apart along a length of the carrier body. The lead body 808 extends proximally from electrode portion 801 and includes an anchor 810 with a proximal lead portion 812 configured for extension to and electrical connection to an IPG (55 in FIG. 1 or 109 in FIG. 2).

The electrode strip 815 has a length (L2) substantially greater than a diameter of a nerve, and sufficient to extend across a diameter of a nerve 840 and outward from both sides of the nerve 840, as shown in at least FIGS. 26-27. In one embodiment, the length (L2) is at least twice the diameter of the nerve. In another embodiments, the length (L2) is at least three times the diameter of the nerve, such that with an expected nerve diameter of about 3 millimeters, the electrode strip 815 has a length (L2) of about 9 millimeters. In this embodiment, about 3 millimeters of the full length of the electrode strip 815 would be in close proximity or contact with the nerve 840 while about 3 millimeters of the length of the electrode strip 815 would extend outward from each side of the nerve 840, as schematically illustrated in FIGS. 26-27. In some embodiments, electrode strip 840 has a width (W4) of about 3 millimeter, which facilitates a minimally invasive implantation method in some embodiments (as will be later described in more detail in association with FIGS. 30-32). In comparison, a conventional cuff electrode might typically have a width of about 9 millimeters.

In use, the electrode portion 801 is delivered to an intended stimulation site along the hypoglossal nerve 840 and with the electrode strip 815 having a generally perpendicular orientation relative to a longitudinal axis (represented by line A) of the nerve 840 (in the region of the intended stimulation site), as shown in FIG. 26. In one embodiment, as illustrated in the sectional view of FIG. 27, the electrode portion 801 is positioned so that the electrodes 820 of electrode strip 815 faces toward nerve 840 to apply the stimulation signal onto the nerve 840. Moreover, in some embodiments, each electrode 582 is independently programmable or controllable via IPG 55 (FIG. 1) in a manner substantially similar to previously described embodiments to allow control and adjustment over the stimulation signal without re-positioning the electrode strip 815. In addition, an insulative shield 804 is interposed between the nerve 840 and skin 830 (and underlying muscle 832) such that the shield 804 permits application of the stimulation signal on the nerve 840 while preventing application of the stimulation signal on the skin 830.

In this arrangement, nerve 840 is sandwiched between the electrode strip 815 and insulative shield 804 and the electrode portion 801 is deployed so that at least a portion of the electrode strip 806 extends, in close proximity to or in close contact with, about the outer surface of the nerve 840, as shown in the sectional view of FIG. 27. However, in this sandwiched arrangement, each of the electrode strip 815 and shield 804 are secured independently relative to the surrounding tissue such that neither electrode strip 815 nor shield 804 are secured to the nerve 840. For example, in one embodiment, electrode strip 815 is secured at each of its ends, via anchors (represented by x 878 and x 879 in FIG. 26), relative to the surrounding tissue and independent of nerve 840. With the generally perpendicular orientation of both the electrode strip 815 and the shield 804, this configuration permits movement of the nerve 840 in a lateral direction (represented by arrow M) relative to both the electrode strip 815 and the shield 804, thereby accommodating shifting of the nerve 840 as the neck of the patient moves through a wide range of motion through many different positions.

With this in mind, upon lateral movement of nerve (along arrow M), both the electrode strip 815 and shield 804 remain stationary such that the sandwiched arrangement is maintained even when nerve 840 moves. Accordingly, because of the electrode strip 815 has a length (L2) that is substantially longer than the diameter of nerve 840, in any lateral position of the nerve 840 (within a natural, limited range of motion) the electrode strip 815 remains in a position to apply an efficacious stimulation signal to nerve 840. Similarly, because the shield 804 has length (L3) substantially longer than the diameter of nerve 840 and substantially longer than the length (L2) of the electrode strip 815, the shield is always positioned to block application of the stimulation signal to the skin 830 (and underlying sensory nerves). In one embodiment, shield 804 defines an area substantially greater than an area of an electrical field produced by electrodes 820 toward a skin surface.

While the electrode portion 801 extends generally perpendicular to the longitudinal axis of the nerve 840 (at the stimulation site), in some embodiments the lead body 808 extends generally parallel to the longitudinal axis of the nerve 840 to follow a path toward the IPG 55 (FIG. 1). As previously noted, the lead body 808 includes an anchor 810 to permit securely anchoring the lead body 808 (and therefore the electrode portion 801 as well) relative to the anatomical structures and tissues nearby to the nerve 840. From the anchor 810, a proximal portion 812 of the lead body 808 extends further toward the IPG 55 (FIG. 1) via a subcutaneous tunnel.

In some embodiments, the application of a perpendicular orientation of an electrode strip (e.g. electrode strip 815) relative to nerve 840 is used with other cuff-less electrode configurations. For example, embodiments associated with FIGS. 11-14C can be deployed to orient the electrode portion 565 to be generally perpendicular to the nerve such that the series of electrodes 582 are aligned transverse to a longitudinal axis of the target nerve without a cuff encircling the circumference of the nerve 840. It will be understood that the number of electrode contacts will be adjusted, as appropriate, in the electrode portion 565 to insure capture of the nerve throughout a full cross-section (or diameter) of the nerve.

In further reference to FIGS. 25-29, in some embodiments, electrode portion 801 includes one or more anchoring mechanisms. Accordingly, FIG. 28 is a top plan view of an electrode portion 850 including a series of electrode contacts 820, a distal end 852, and a proximal end 854. At distal end 852, one or more loops (or other securing elements) 860 are provided to enable suturing or otherwise fastening the distal end 852 relative to surrounding tissue adjacent the nerve 840. Similarly, at proximal end 854, one or more loops (or other securing elements) 870, 872 are provided to enable suturing or otherwise fastening the proximal end 854 relative to surrounding tissue adjacent the nerve 840. In this way, the electrode strip 850 is securable in a stable position close to nerve 840 (but independently of the nerve) without being secured to the nerve 840 itself and/or without encircling the nerve 840.

In some other embodiments, as schematically illustrated in the sectional view of FIG. 29, electrode strip 815 and shield 804 are secured together. In these embodiments, the sandwiched configuration of electrode strip 815 and shield 804 is maintained relative to nerve 840 to thereby permit lateral movement (directional arrow M) of nerve 840 while still providing electrical stimulation of nerve 840 via electrode strip 815 and while still protecting skin 830 via shield 804. In particular, fastening mechanism 870 includes a first component 872 and a second component 874, with each respective component 872, 874 sized to extend between the electrode strip 815 and the shield 804. In one non-limiting aspect, by providing first component 872 on one lateral side of nerve 840 (connected to the first ends of the respective strip and shield) and by providing second component 874 on an opposite lateral side of nerve 840 (connected to the second ends of the respective strip and shield), the fastening mechanism 870 provides a lateral boundary or barrier to insure that nerve 840 will remain between electrode strip 815 and shield 804 while permitting lateral movement of nerve 840. In other embodiments, only one end of the respective electrode strip 815 and the shield 804 are secured together, leaving the other end open.

In one embodiment, the first component 872 of securing mechanism 870 comprises a buckle-belt mechanism that is connectable to the distal end 817 of electrode strip 815 and connectable to the distal end 805 of the shield 804. Likewise, the second component 874 comprises a buckle-belt mechanism that is connectable to the proximal end 816 of electrode strip 815 and connectable to the proximal end 807 of the shield 804.

Figure 30:
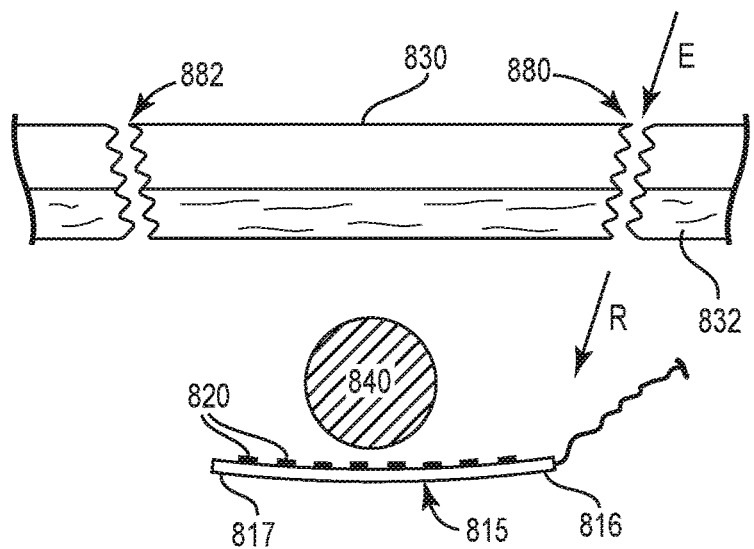
FIG. 30 is a sectional view schematically illustrating one aspect of a method of percutaneous access for a stimulation system, according to an embodiment of the present disclosure.
Figure 31:
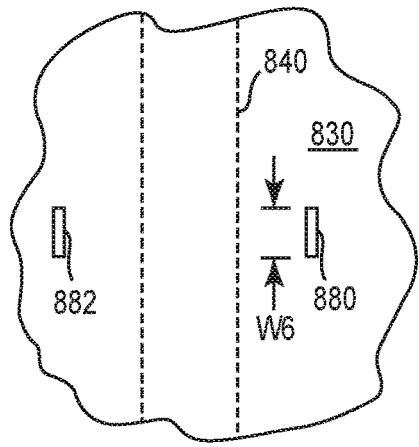
FIG. 31 is a top elevational view schematically illustrating one aspect of the method of percutaneous access, according to an embodiment of the present disclosure.
Figure 32:
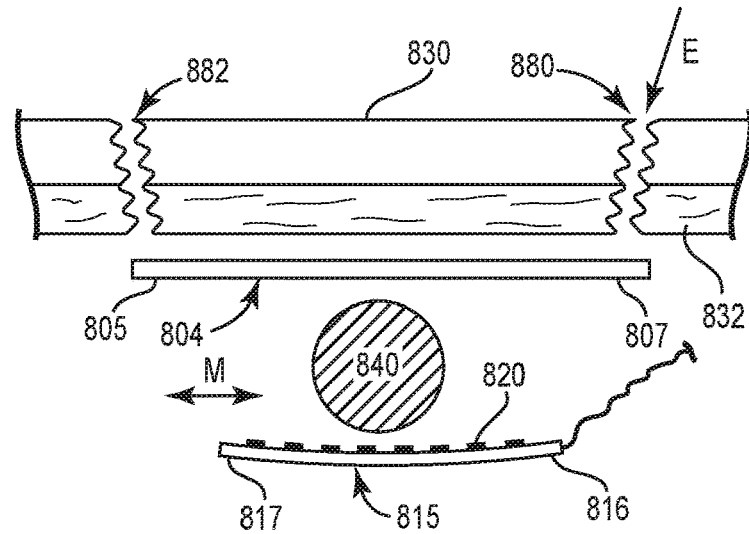
FIG. 32 is a sectional view schematically illustrating another aspect of the method of percutaneous access, according to an embodiment of the present disclosure.

In some embodiments, the combination of the shield 804 and the electrode strip 815 are delivered percutaneously in a minimally invasive implantation method, as schematically illustrated in FIGS. 30-32. In particular, because the electrode strip 815 is quite narrow (e.g., 3 millimeters wide as shown in FIGS. 25-27), the procedure begins via making two small incisions 880, 882 in the skin 830 (and underlying tissues/muscles 832) on opposite lateral sides of the underlying nerve 840, as shown in FIG. 31. At least one of the incisions 880, 882 will have a width (W6) generally corresponding to the width (W4 in FIG. 25) of the electrode strip 815. Using a forceps (not shown), the electrode strip 815 is maneuvered through incision 880 and via incision 882 (as represented via arrows E and R) until the electrode strip 815 is in position underneath nerve 840 with electrode contacts 820 in close contact with the nerve 840 and facing skin 830, as shown in FIG. 30. Next, using a similar technique involving incisions 880 and/or 882, the shield 804 is introduced into a position interposed between nerve 840 and skin 830. If necessary, either incision 880, 882 can be widened slightly to accommodate introduction of the larger width (W5) of shield 804 through the respective incision. With this minimally invasive method of implantation, the sandwiched configuration of the electrode strip 815 and the shield 804 relative to the nerve 840 is achieved with minimal disruption to the skin and tissues above and near the nerve 840. Accordingly, the combination of the electrode strip 815 and the shield 804 enable a minimally invasive method of implanting those elements while also providing a stimulation system that minimally impacts the natural state of the nerve by acting as a cuff-less electrode.

Several different embodiments have been described in association with FIGS. 1-14, in which an IPG 55 is implanted in a pectoral region and in which a sensor electrode(s) and a stimulation electrode(s) (extending from the IPG 55) are delivered percutaneously to sense respiratory patterns and to apply a stimulation signal, respectively. In addition, several embodiments of stimulation electrode arrays (and associated anchor mechanisms) have been described in association with FIGS. 15-32. Moreover, it is understood that in some of these embodiments, a lead is percutaneously placed in each side of the body (left and right) such that bilateral (simultaneous or alternating) stimulation takes place on the left and/or right hypoglossal nerve (or other target nerve). With these various embodiments in mind, it is further understood that among those embodiments, several configurations are provided in which at least two electrodes are spaced apart in the body in the vicinity of the upper airway such that an impedance is measurable between the two spaced apart electrodes to provide an indication of airway patency (e.g., opening and/or closing of the upper airway). In some configurations, the spaced electrodes are both stimulation electrodes, while in other configurations, the spaced apart electrodes comprise one stimulation electrode and one respiratory sensor electrode. In yet other configurations, the two spaced apart electrodes (used for measuring an impedance indicative of airway patency) include one of the electrodes comprising at least one of a stimulation electrode and a respiratory sensor electrode and the other one of the electrodes comprising an electrode formed by an electrically conductive portion of a case or housing of the IPG 55.

Moreover, in some embodiments, the respective electrode portions provide a dual function in that each electrode provides a respiratory sensing function or a stimulation function as well as acting as a part of a pair of impedance sensing electrodes. On the other hand, in other embodiments, at least one electrode of the pair of impedance sensing electrodes does not also act to sense respiration (e.g. inspiration) or to stimulate but rather is dedicated for use in sensing impedance to detect or indicate a degree of airway patency.

At least some embodiments of the percutaneously-delivered electrode portions (described herein) enable precise location of an electrode portion adjacent to an optimal neurostimulation site because the percutaneous approach enables the surgeon to vary the position of an electrode portion of a stimulation lead along the length of the hypoglossal nerve. In addition, this precise placement is performed in a minimally invasive manner unlike the anatomically disruptive conventional cut-down procedure for placing stimulation leads. The methods and systems of the present disclosure allows the surgeon to identify a precise optimal stimulation site that causes contraction of one or more specific muscles (suited to restore airway patency) prior to fixing the location of the electrode portion relative to the target nerve.

Embodiments of the present disclosure provide an implantable system to provide therapeutic solutions for patients diagnosed with obstructive sleep apnea. The system is designed to stimulate the hypoglossal nerve during inspiration thereby preventing occlusions in the upper airway during sleep.

While at least one exemplary embodiment has been presented in the foregoing detailed description, it should be appreciated that variations exist. It should also be appreciated that the exemplary embodiment or exemplary embodiments are only examples, and are not intended to limit the scope, applicability, or configuration of the present disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the present disclosure as set forth in the appended claims and the legal equivalents thereof.

The invention claimed is:

1. A method of implanting comprising:
   inserting, via a single skin incision, a stimulation element into a head-and-neck region adjacent an upper airway patency-related nerve; and
   advancing the stimulation element through tissue underlying the single skin incision and positioning the stimulation element within the head-and-neck region to establish engagement of an electrode array of the stimulation element relative to a target portion of the upper airway patency-related nerve;
   employing an introduction tool to carry the stimulation element during the inserting and advancing, wherein the stimulation element resides within the introduction tool during the inserting and the advancing and wherein the stimulation at least one anchoring element, and wherein the introduction tool includes:

an engagement mechanism at a distal portion of the introduction tool; and a trigger at a proximal portion of the introduction tool to cause the selective deployment of the engagement mechanism; and upon final positioning of the stimulation element relative to the target portion of the upper airway patency-related nerve, selectively deploying the engagement mechanism of the introduction tool to cause the at least one anchoring element, coupled to the stimulation element, to securely engage non-nerve surrounding tissue to maintain engagement of the stimulation element relative to the target portion of the upper airway patency-related nerve.

2. The method of claim 1, wherein the positioning comprises:

prior to the securely engaging, selectively initially positioning the electrode array of the stimulation element along a length of the target portion of the upper airway patency-related nerve, while stimulating the upper airway patency-related nerve, to identify a target stimulation site.

3. The method of claim 1, comprising:

withdrawing the introduction tool via the single skin incision while leaving the stimulation element positioned, via the at least one anchoring element, in engagement relative to the target portion of the upper airway patency-related nerve.

4. The method of claim 1, wherein the at least one anchoring element comprises a barb detachably connected to a portion of the stimulation element.

5. The method of claim 1, comprising:

arranging a carrier body of the stimulation element to include:

a first portion comprising the electrode array; and a second portion comprising a non-conductive portion supporting the electrode array; and a non-nerve securing structure located at least one of:

at least one of opposite side portions of the carrier body; or at least one of opposite end portions of the carrier body; and maintaining engagement of the electrode array relative to the target portion of the upper airway patency-related nerve via securing a respective one of the opposite side portions and end portions, via the at least one anchoring element, relative to the non-nerve surrounding tissue.

6. The method of claim 5, arranging the non-nerve securing structure as a loop to which the at least one anchoring element may be coupled; and engaging the non-nerve surrounding tissue via the at least one anchoring element to secure the loop to the non-nerve surrounding tissue.

7. The method of claim 1, wherein the introduction tool comprises a conduit.

\* \* \* \* \*